US008409565B2

(12) United States Patent
Levi-Schaffer et al.

(10) Patent No.: US 8,409,565 B2
(45) Date of Patent: Apr. 2, 2013

(54) THERAPEUTIC TARGET AND DIAGNOSTIC MARKER FOR ASTHMA AND RELATED CONDITIONS

(76) Inventors: Francesca Levi-Schaffer, Jerusalem (IL); Ido Bachelet, Modi'in (IL); Ariel Munitz, Jerusalem (IL); Marc E. Rothenberg, Cincinnati, OH (US)

(*) Notice: Subject to any disclaimer, the term of this patent is extended or adjusted under 35 U.S.C. 154(b) by 556 days.

(21) Appl. No.: 11/705,829

(22) Filed: Feb. 14, 2007

(65) Prior Publication Data
US 2007/0212353 A1    Sep. 13, 2007

Related U.S. Application Data

(60) Provisional application No. 60/772,883, filed on Feb. 14, 2006.

(51) Int. Cl.
*A61K 38/00* (2006.01)
*A61K 39/00* (2006.01)
*A61K 39/395* (2006.01)

(52) U.S. Cl. ............... 424/130.1; 424/133.1; 424/139.1; 514/1.1

(58) Field of Classification Search ......................... None
See application file for complete search history.

(56) References Cited

U.S. PATENT DOCUMENTS

| 6,753,348 B2 * | 6/2004 | Uckun et al. ............ 514/521 |
| 2002/0055514 A1 * | 5/2002 | Uckun et al. ............ 514/259 |
| 2007/0178072 A1 * | 8/2007 | Watanabe ............ 424/93.7 |

OTHER PUBLICATIONS

Chavin et al. 'Anti-CD48 (murine CD2 ligand) mAbs suppress cell mediated immunity in vivo.' INt. Immunol. 6(5):701-709, 1994.*
Akbari et al. 'Role of regulatory T cells in allergy and asthma.' Curr. Opin. Immunol. 15(6):627-633, 2003.*
Chavin et al. 'Anti-CD48 (murine CD2 ligand) mAbs suppress cell mediated immunity in vivo.' Int. Immunol. 6(5):701-9, 1994.*
Bai et al. 'CD2 is a Dominant Target for Allogeneic Responses.' Am J Transplant. 2(7):618-26, 2002.*
Zimmermann et al., "Dissection of Experimental Asthma with DNA Microarray Analysis Identifies Arginase in Asthma Pathogenesis", The Journal of Clinical Investigation, vol. 111, pp. 1863-1874 (2003).
Munitz et al., "2B4 (CD244) Is Expressed and Functional on Human Eosinophils", The Journal of Immunology, vol. 174, pp. 110-118 (2005).
Brown et al., "2B4, the Natural Killer and T Cell Immunoglobulin Superfamily Surface Protein, Is a Ligand for CD48", The Journal of Experimental Medicine, vol. 188, No. 11, pp. 2083-2090 (1998).
Klyushnenkova et al., "CD48 Delivers an Accessory Signal for CD40-Mediated Activation of Human B Cells", Cellular Immunology, vol. 174, No. 1, pp. 90-98 (1996).
Rader et al., "A Phage Display Approach for Rapid Antibody Humanization: Designed Combinatorial V Gene Libraries", Proc. Natl. Acad. Sci. USA, vol. 95, pp. 8910-8915 (1998).
Mateo et al., "Humanization of a Mouse Monoclonal Antibody that Blocks the Epidermal Growth Factor Receptor: Recovery of Antagonistic Activity", Immunotechnology, vol. 3, pp. 71-81 (1997).
Giembycz et al., "Pharmacology of the Eosinophil", Pharmacological Reviews, vol. 51, No. 2, pp. 213-340 (1999).
Fulkerson et al., "Pulmonary Chemokine Expression is Coordinately Regulated by STAT1, STAT6, and IFN-γ", The Journal of Immunology, vol. 173, pp. 7565-7574 (2004).
Rothenberg et al., "Human Eosinophils Have Prolonged Survival, Enhanced Functional Properties, and Become Hypodense When Exposed to Human Interleukin 3", J. Clin. Invest., vol. 81, pp. 1986-1992 (1988).
Patel et al. "A Molecular Framework for Two-Step T Cell Signaling: Lck Src Homology 3 Mutations Discriminate Distinctly Regulated Lipid Raft Reorganization Events", The Journal of Immunology, vol. 166, pp. 754-764 (2001).
Stefanova et al., "GPI-Anchored Cell-Surface Molecules Complexed to Protein Tyrosine Kinases", Science, vol. 254, pp. 1016-1019 (1991).
Yokoyama et al., "Expression of the Blast-1 Activation/Adhesion Molecule and its Identification as CD48", The Journal of Immunology, vol. 146, No. 7, pp. 2192-2200 (1991).
Ianelli et al., "CD48 Binds to Heparan Sulfate on the Surface of Epithelial Cells", The Journal of Biological Chemistry, vol. 273, No. 36, pp. 23367-23375 (1998).
Mishra, A. et al., "Fundamental Signals That Regulate Eosinophil Homing to the Gastrointestinal Tract", The Journal of Clinical Investigation, vol. 103, No. 12, pp. 1719-1727 (1999).
Horejsi et al., "GPI-Microdomains: A Role in Signaling Via Immunoreceptors", Immunology Today, vol. 20, pp. 356-361 (1999).
Van Rijt et al., "A Rapid Flow Cytometric Method for Determining the Cellular Composition of Bronchoalveolar Lavage Fluid Cells in Mouse Models of Asthma", Journal of Immunological Methods, vol. 288, pp. 111-121 (2004).
Southam et al., "Increased Eosinophil-lineage Committed Progenitors in the Lung of Allergen-Challenged Mice", J. Allergy Clin. Immunol., vol. 115, pp. 95-102 (2005).
Finkelman et al., "Anti-Cytokine Antibodies as Carrier Proteins", The Journal of Immunology, vol. 151, No. 3 151: 1235-1244 (1993).
Bochner, B. S., "Verdict in the Case of Therapies Versus Eosinophils: The Jury is Still Out", J. Allergy Clin. Immunol., vol. 113, pp. 3-9 (2004).
Finkelman et al., "Developmental of an Assay to Measure in Vivo Cytokine Production in the Mouse", International Immunology, vol. 11, No. 11, pp. 1811-1818 (1999).
Munitz et al., "The Inhibitory Receptor IRp60 (CD300a) Suppresses the Effects of IL-5, GM-CSF and Eotaxin on Human Peripheral Blood Eosinophils", Blood, Oct. 27, 2005.

*Primary Examiner* — Nora Rooney
(74) *Attorney, Agent, or Firm* — Browdy and Neimark, PLLC

(57) ABSTRACT

CD48, a surface-marker molecule present in eosinophils, is disclosed herein as a key molecule in allergic conditions, particularly in allergic airway inflammations like asthma, allergy and nasal polyposis. CD48 is thus presented as a target molecule in the treatment of said conditions. In addition, diagnostic methods, and a kit for the diagnosis of allergic inflammatory conditions are described, based on the detection of CD48 expression.

8 Claims, 21 Drawing Sheets

THERAPEUTIC TARGET AND DIAGNOSTIC MARKER FOR ASTHMA AND RELATED CONDITIONS

FIELD OF THE INVENTION

The present invention relates generally to the field of allergic conditions. In particular, the present invention is concerned with providing a marker for the diagnosis of allergic inflammation, particularly, allergic airway inflammation such as asthma and related conditions, as well as with agents for the treatment of said conditions.

BACKGROUND OF THE INVENTION

All publications mentioned throughout this application are fully incorporated herein by reference, including all references cited therein.

Asthma is a chronic and complex inflammatory disease of the airways characterized by airflow obstruction, bronchial hyper-responsiveness (BHR) and airway inflammation. It is the most common chronic illness of childhood, with up to 20% of children affected in some Western countries. The incidence as well as the number of hospital admissions attributable to asthma continues to rise in both adults and children. Over the last decade the importance of airway inflammation in the disease process has been carefully investigated, and revealed that the asthmatic tissue is characterized by the accumulation of a large number of inflammatory cells (e.g. eosinophils, neutrophils, basophils, mast cells), increased mucus production, epithelial shedding and hypertrophy, mucus, smooth muscle cell hypertrophy and sub-mucosal mucus glands hyperplasia/metaplasia and fibrosis. Notably, chronic inflammation of the asthmatic lung leads to structural changes, that in turn exacerbate the hyperresponsiveness observed in this disease. While these findings have provided the rationale for the development of multiple therapeutic agents that interfere with specific inflammatory pathways, the development of the asthma phenotype is likely to be related to a complex interplay of a large number of genes combined with environmental factors. Recent genome searches have revealed that at least 19 genes contribute to asthma susceptibility and microarray studies of asthmatic tissue revealed the involvement of hundreds of genes. Moreover, microarray analysis has recently demonstrated increased expression of 291 genes that were commonly involved in murine disease pathogenesis rather than to a particular mode of disease induction [Zimmermann, N. et al. (2003) *J. Clin. Invest.* 111: 1863-74]. Therefore, a central issue still under pursuit is identification of fundamental molecules/pathways that govern the processes underlying inflammation in asthma. Nonetheless, no asthma drug so far has been able to inhibit the initial steps of the signaling cascade of this agonizing medical condition. Therapeutic drugs for asthma are usually directed to the symptoms, i.e., ex post facto of the asthma attack.

Eosinophils are thought to be key effector cells in asthma by the release of basic granule proteins, membrane phospholipid metabolites and a variety of cytokines. For example, the eosinophil basic proteins have been found to be highly toxic in vitro to respiratory epithelial cells, at concentrations detected in biological fluid from patients with asthma. Furthermore, eosinophils produce matrix metalloproteinase (MMP)-9, tissue inhibitor of matrix metalloproteinase (TIMP)-½, contain heparanase and are a source for vascular endothelial growth factor (VEGF), platelet derived growth factor (PDGF) and b-fibroblast growth factor (b-FGF), indicating their role in asthma-associated symptoms.

Since a central question concerning eosinophils is to understand the mechanisms by which these cells get activated or inhibited and whether a "disease-specific" activator exists, the inventors screened eosinophils with monoclonal antibodies (mAbs) produced to recognize epitopes expressed on T lymphocytes and NK cells, preferably. The inventors found that human eosinophils express 2B4 [Munitz, A. et al. (2005) *J. Immunol.* 174: 110-118], and that 2B4 is a functional activator receptor on these cells in vitro, suggesting that a complex network of activating signals regulate the immunological or inflammatory responses coordinated by eosinophils.

CD48 is a glycosyl-phosphatidyl-inositol (GPI) anchored protein belonging to the CD2-subfamily, which is involved in lymphocyte adhesion, activation and co-stimulation. It is expressed mainly on hematopoietic cells and exists in both a membrane-associated and a soluble form. Studies on CD48-deficient mice indicate that CD48 has a broad immunological importance. In fact, CD48 has been described to interact with extracellular matrix components such as heparin sulfate, facilitate cell adhesion, innate responses to bacterial infection and graft rejection and provide co-stimulatory signals to T and B lymphocytes. Furthermore, CD48 has a distinctive role in orchestrating mast cell innate responses towards *E. coli*. Besides, CD48 is a low affinity ligand for CD2 but a high affinity ligand for 2B4 [Brown, M. H. et al. (1998) *J. Exp. Med.* 188(11):2083-90]. CD48-2B4 interactions can modulate T cell, B cell and NK cell functions and cross-talk. Studies with 2B4 gene-targeted mice, demonstrated that 2B4-CD48 interactions are essential for expansion and activation of murine NK cells. The absence of functional 2B4-CD48 interactions impairs NK cell cytotoxic response and IFN-γ release upon tumor target exposure. Furthermore, activated NK cells significantly increase the CD3-dependent proliferation of $CD8^+$ and $CD4^+$ T cells by a 2B4-CD48 dependent mechanism. n. Furthermore, cross-linking of CD48 on the surface of rodent T lymphocytes induced mobilization of the intracellular calcium inositol triphosphate concentration. T cell activation via CD48 combined with CD3 induced enhanced IL-2 release, T cell receptor signaling and cytoskeletal reorganization. Furthermore, cross-linking of CD48 on the surface of rat or murine B cells induced strong homotypic adhesion suggesting that this molecule can be involved in B cell activation. In humans, cross-linking of CD48 on purified tonsillar B cells significantly increased CD40-mediated activation. Additionally, CD48, in combination with IL-4 and/or IL-10 is able to induce B cell aggregation, proliferation and IgG secretion [Klyushnenkova, E. N. et al. (1996) *Cell Immunol.* 174(1):90-8].

SUMMARY OF THE INVENTION

In view of the fact that allergic airway condition and specifically, asthma is a Th2 associated process, it is worthwhile mentioning that until the present invention, the contribution of CD48 has not been explored in Th2 settings. In this study, the inventors investigated the contribution of CD48 and its ligands to allergic eosinophilic airway inflammation. Therefore, the present invention show for the first time that CD48 is up regulated in two murine models of allergic eosinophilic airway inflammation. More particularly, the present invention demonstrates that CD48 is up-regulated in two mouse models of experimental asthma. The findings indicate that CD48 over-expression is at least partially regulated by IL-3. Furthermore, neutralization of CD48 in allergen-challenged mice resulted in abrogation of lung inflammation, airway smooth muscle thickening, mucus production and goblet cell hyperplasia as well as in decreased eosinophilia in the BALF (bronchoalveolar lavage fluid) and spleen. In addition, neutralization of CD48 diminished chemokine and cytokine levels in the BALF. Finally, the expression of CD48 was upregulated in eosinophils from atopic asthmatics vs. normal controls, pointing out the critical involvement of this molecule in asthma. Furthermore, experiments with anti-CD48, anti-CD2 and anti-2B4 neutralizing mAbs, demonstrate that CD48 is critically involved in allergic eosinophilic airway inflammation.

Thus, the present invention provides CD48 as a molecular marker and as a target for therapeutic and diagnostic methods for allergic conditions, specifically, asthma and asthmatic related conditions.

It is therefore one object of the invention to provide methods of treating an allergic condition, specifically, an allergic-eosinophilic airway inflammation such as asthma and asthma related disorders, by specifically inhibiting the activity or the expression of CD48.

Another object of the invention relates to a therapeutic composition for the treatment of allergic inflammation, particularly, allergic airway inflammation, using an anti-CD48 agent such as an anti-CD48 antibody, an antibody against a down-stream molecule of the CD48 stimulatory pathway, or a nucleic acid molecule specifically targeted to decrease CD48 expression or to decrease the expression of a down-stream member molecule of the CD48 stimulatory pathway.

In another object, the invention provides a diagnostic method for detection of an allergic condition in a subject. This method involves determining CD48 levels of expression by a suitable means either in the protein or nucleic acids level. Whereby elevated expression of CD48 in comparison to a negative control, indicates the presence of such condition.

Other objects, purposes and advantages of the invention will become apparent as the description proceeds.

In a first aspect, the invention relates to a method of treating an allergic condition, particularly, an allergic inflammation, specifically, airway inflammation such as asthma and nasal polyposis, atopic dermatitis, conjunctivitis and intestinal allergy. This method comprises administering a therapeutically effective amount of an anti-CD48 agent which blocks CD48 stimulatory pathway, to a subject in need of such treatment.

According to one embodiment, the anti-CD48 agent used by the method of the invention preferably blocks CD48 stimulatory pathway by inhibiting the activity and/or the expression of CD48 or of a down-stream member molecule of the CD48 stimulatory pathway. The anti-CD48 agent used by the invention may be a protein-based molecule, such as anti-CD48 antibody, which specifically binds to CD48.

The anti CD48 agent may also be an antagonist of the CD48 stimulatory pathway, capable of decreasing or blocking an agonist of said pathway, in a competitive or non-competitive manner.

Alternatively, the anti-CD48 agent may be a nucleic acid based molecule such as, antisense oligonucleotide specific to the CD48 sequence, a ribozyme having catalytic activity (such as cleavage) that renders the CD48 inactive, an interfering RNA (RNAi) such as small interfering RNA (siRNA), or a microRNA capable of preventing the expression (transcription and translation, respectively) of the CD48 into protein.

The invention further provides a method of inhibiting the activity and/or expression of CD48 in cells of a subject in need thereof. This method comprises the step of in vivo contacting the cells with an effective amount of an anti-CD48 agent.

According to another aspect, the invention relates to a method for the diagnosis of an allergic condition in a subject. The diagnostic method of the invention comprises the steps of: (a) obtaining a biological sample from said subject; and (b) determining the level of expression of CD48 in said biological sample by a protein-based or a nucleic acid-based detection method. It should be appreciated that elevated expression of CD48, in comparison with negative control, indicates the presence of an allergic condition.

According to one embodiment, the CD48 expression may be detected by a protein-based method comprising the steps of: (i) contacting the examined sample with a CD48 binding agent, preferably, an anti-CD48 antibody; and (ii) measuring the level of binding of the agent to the CD48 protein in the sample by a suitable protein based detection assay. As a non-limiting example, such assay may be immunohistochemical staining, Western blot analysis, immunopercipitation, flow cytometry, ELISA, competition assay, any combination thereof or any other suitable assay.

According to another embodiment, the CD48 expression may be detected by a nucleic acid based detection method such as in-situ hybridization, RT-PCR, nucleic acid based ELISA, RNAse protection assay, Northern blot analysis, any combination thereof or any other nucleic-acid based suitable assay.

In yet another aspect, the invention relates to a kit for the diagnosis of an allergic condition, the kit comprising as follows: an agent for determining the presence of an analyte of interest, wherein said analyte of interest is one of CD48 protein or CD48 mRNA. The kit further comprises calibration means.

*, $p<0.05$; ** $p<0.005$.

Figure 3A:
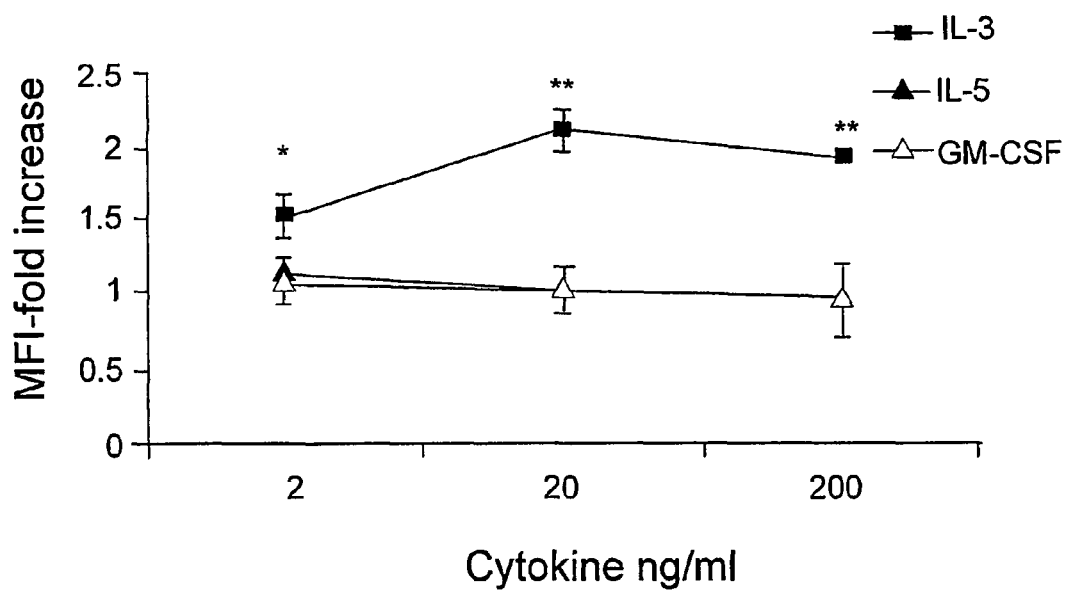
Figure 3B:
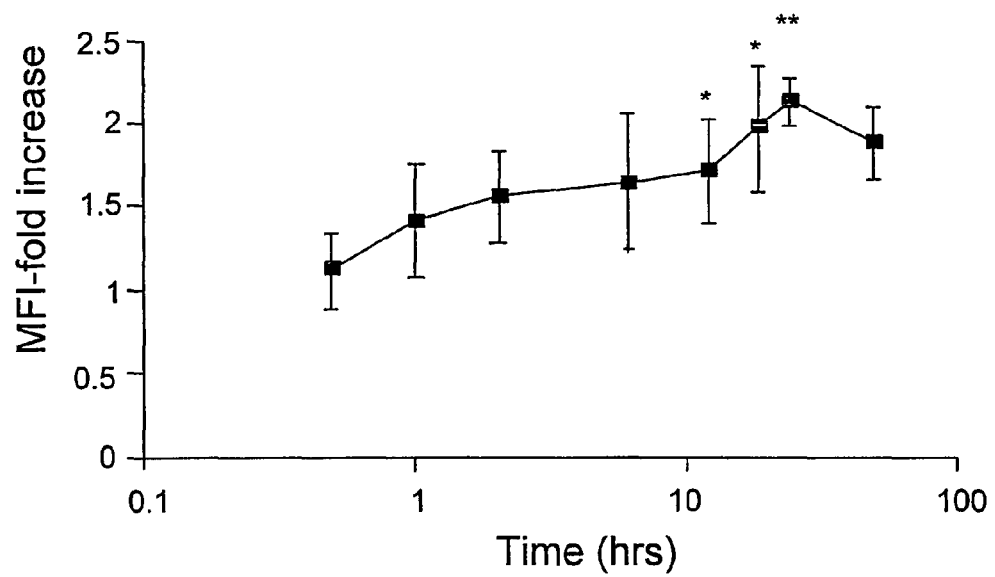

FIG. 3A-B: The Expression of CD48 on Human Peripheral Blood Eosinophils is Regulated by IL-3

Human peripheral blood eosinophils were incubated with the indicated concentrations of rhIL-3, rhIL-5 or rhGM-CSF (A) for 18 hours. Thereafter, cells were washed twice, stained with anti-CD48 mAb followed by goat anti-mouse FITC and analyzed by FACS. Kinetic analysis (B) was performed by incubating human peripheral blood eosinophils with 20 ng/ml of rhIL-3 for the indicated time points. Thereafter, cells were assessed for CD48 expression as described above. Data are presented as mean fluorescent intensity (MFI), each dot represents one donor.

*, $p<0.05$; **$p<0.005$, $n=5$.

FIG. 4A-E: CD48 Expression is Independent of STAT6, IL-4 and IL-13

RNA was extracted from the lungs of wild-type (A-D, left panel), STAT6 deficient [A-B, right panel], IL-13 and IL-4/IL-13 deficient mice (C-D, middle and right panels respectively). Mice that express a tetracycline-inducible IL-13 were fed doxycycline-containing food for the indicated time periods (E). For all Northern blot assays, total RNA was electrophoresed, transferred and hybridized with a radiolabeled sequence confirmed CD48 cDNA probe. The location of 18S RNA is shown. Each lane represents an extract from one separate mouse, EtBr=ethidium bromide.

Figure 5:
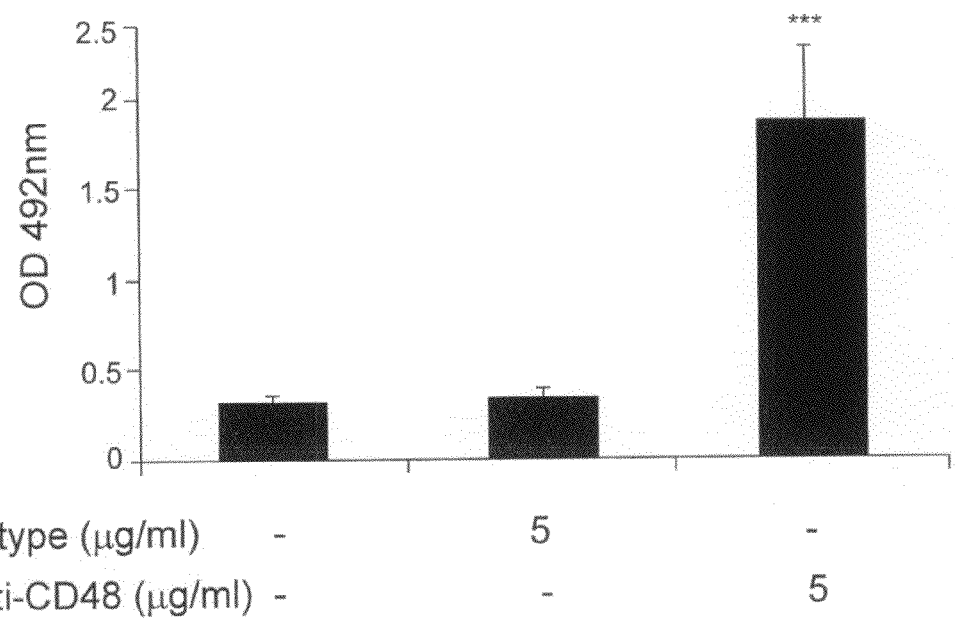

FIG. 5: CD48 Activates Human Peripheral Blood Eosinophils to Release EPO (Eosinophil Peroxidase)

Human peripheral blood eosinophils were cultured in wells pre-coated with sheep anti-mouse F(ab)2 Ab and either iso-type-matched control (isotype) or anti-CD48 mAb (anti-CD48) for 30 min. Culture supernatants were collected and EPO concentration was determined by a colorimetric assay. The data represent the mean±SD of three different experiments performed in triplicate.

***, $p<0.001$, $n=3$.

FIG. 6A-G: IL-3 Regulates CD48 Expression In Vivo IL-3 Mixed with Anti-IL-3 mAb at a 2:1 Molar Ratio, [IL-3C] was administered intranasal (A-D) or systemically (E-F) every other day for 21 days to normal BALB/c mice. Twenty-four hours after the last IL-3C administration, mice were sacrificed, BALF was performed and lungs and spleen excised for differential cell counts as assessed by FACS analysis (A-B, E). For assessment of CD48 expression (C-D, F), BALF and lung cells were stained additionally with anti-CD48 mAb and evaluated by FACS. Eosinophils from the spleen of IL-5 transgenic or wild type mice (G) were stained with anti-CD48 mAb and evaluated by FACS. For (A-B, E) data are presented as total cell number±SD; for (C-D and E-F) data are presented as mean fluorescence intensity [MFI]±SD, from 4-6 mice per group.

*, $p<0.05$;  $p<0.005$, *, $p<0.0001$, $n=3$.

Figure 7A:
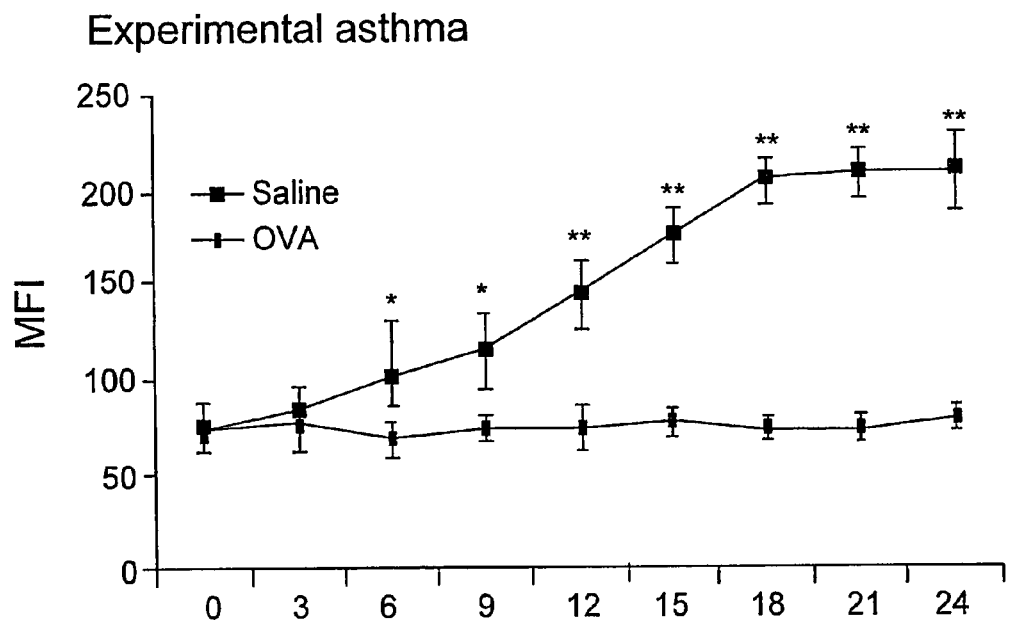
Figure 7B:
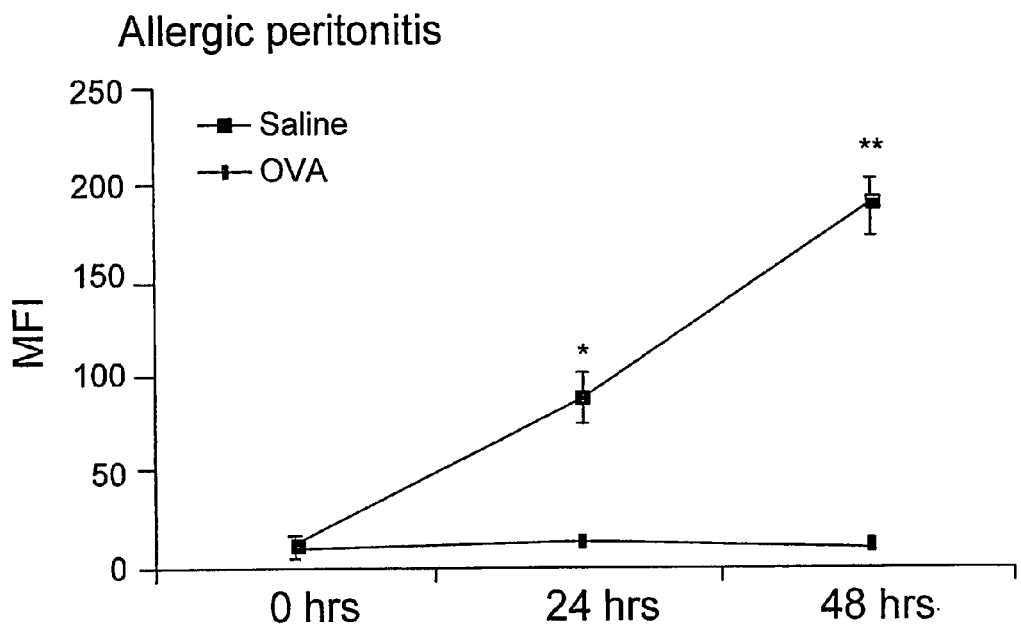

FIG. 7A-B: CD48 is Upregulated on Murine Eosinophils in Experimental Asthma and in Allergic Peritonitis OVA/alum sensitized mice were challenged with OVA. Mice were sacrificed at the indicated time points after the last allergen challenge and BALF (A) or peritoneal lavage (B) was performed. The cells were stained with PE-labeled anti-CD48 and FITC-labeled anti-CCR3. CCR3$^+$/SSC$^{high}$ cells were gated and analyzed for CD48 expression. Data are expressed as mean fluorescence intensity [MFI]±SD from 4-6 mice per group.

*, $p<0.05$; ** $p<0.005$, $n=3$.

Figure 8A:
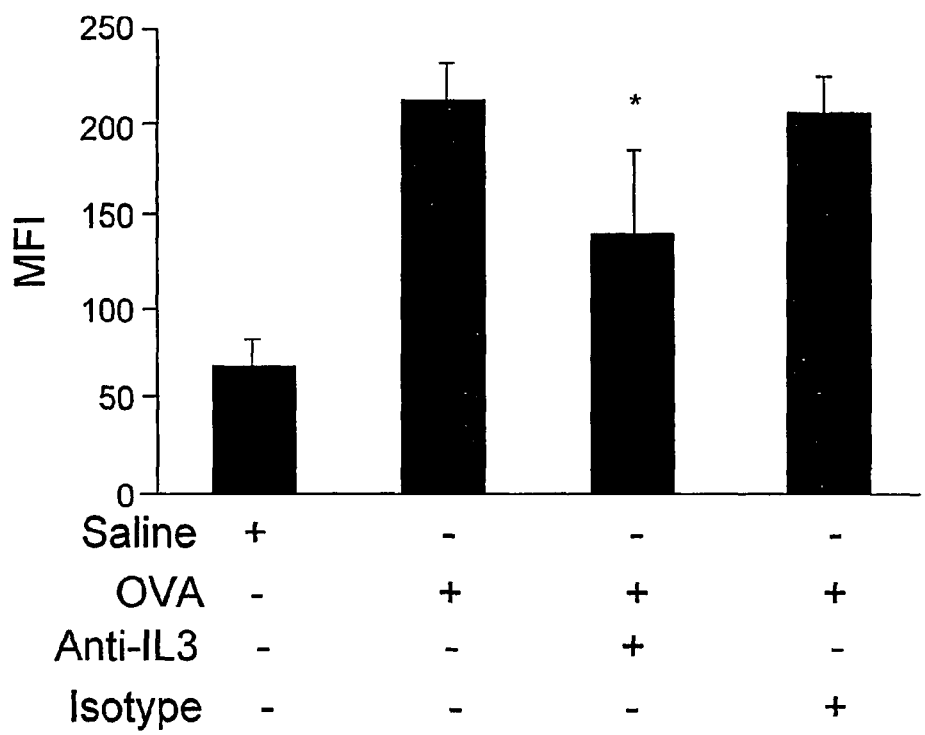
Figure 8B:
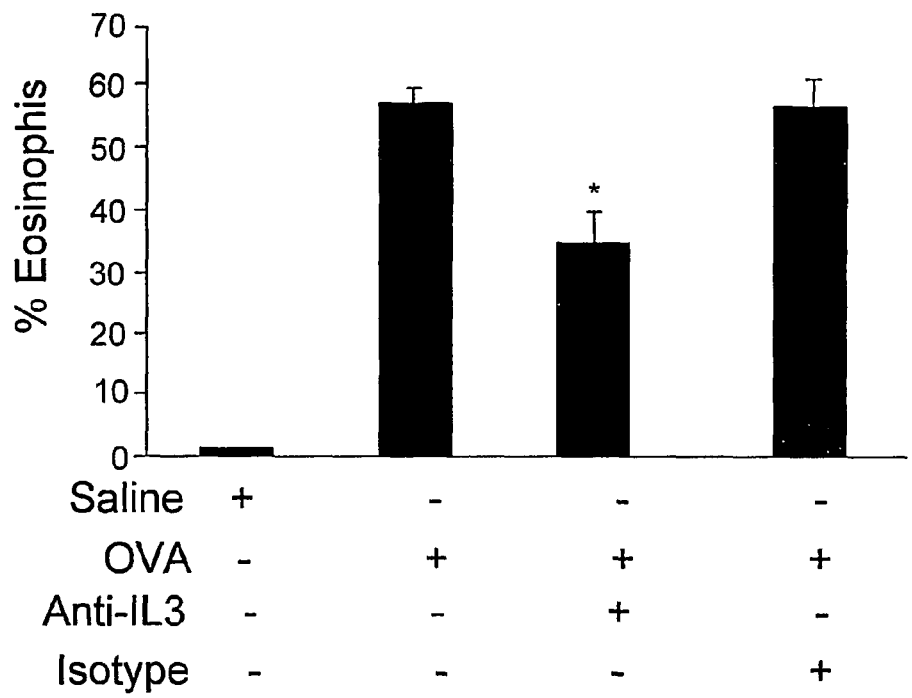
Figure 8C:
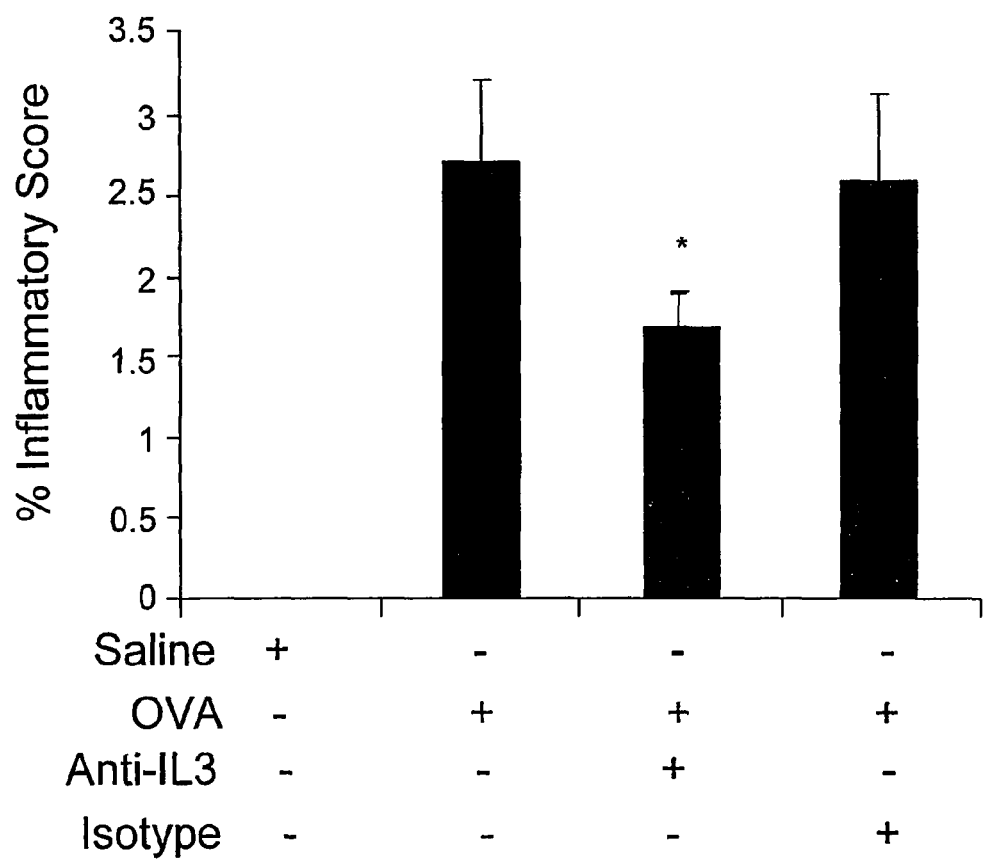

FIG. 8A-C: Neutralization of IL-3 in Murine Experimental Asthma Reduces CD48 Expression OVA/alum sensitized mice were treated with anti-IL-3 mAb or an isotype-matched control mAb (2 mg/mouse) on day 23 (24 hrs before allergen challenge) and days 24 and 27 (1 hr before allergen challenge). BALF was performed and lungs were excised, 24 hrs after the last allergen challenge. BALF cells were stained with PE-labeled anti-CD48 and FITC-labeled anti-CCR3. CCR3$^+$/SSC$^{high}$ cells were gated and analyzed for CD48 expression (A) and percentage of eosinophils, defined as CCR3$^+$/SSC$^{high}$ cells (B). Lungs were fixed, paraffin embedded, stained for H&E and scored as described (C). In (A and B) data are expressed as mean fluorescence intensity [MFI]±SD or percentage of cells, respectively. In (C) data are expressed as mean inflammatory score±SD. All data were obtained from 4-6 mice per group.

$n=3$ *, $p<0.05$.

Figure 9:
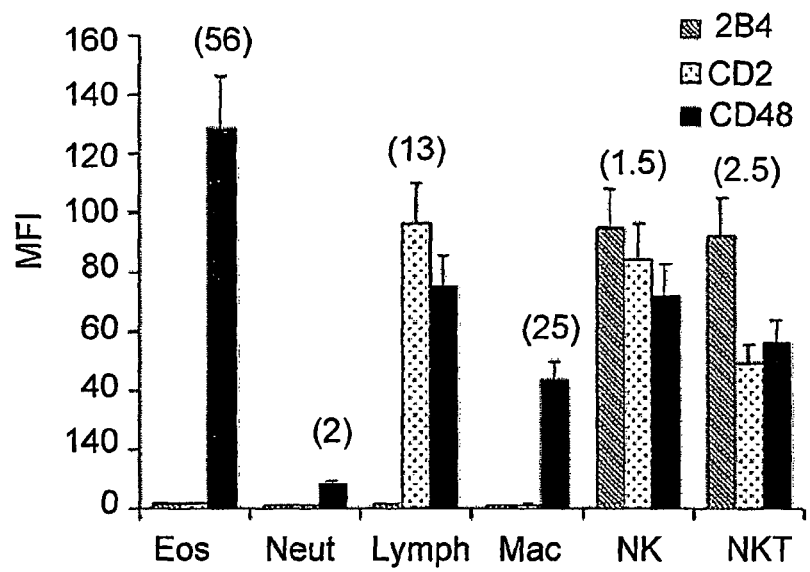

FIG. 9: Cellular Source of CD48, CD2 and 2B4 in the Lungs

OVA/alum sensitized mice were challenged with OVA. Eighteen hours after the last allergen challenge the lungs were harvested and expression of CD48, CD2 and 2B4 was analyzed on various cell types. The data are represented as ΔMFI±SD $n=3$. Eos-eosinophils, Neut-neutrophils, Lymph-CD4$^+$ lymphocytes, Mac-macrophages, NK-NK cells, NKT-NKT cells, parentheses indicate the percentage of the indicated cell in the BALF.

FIG. 10A-G: Neutralization of CD48 Attenuates Eosinophilic Inflammation, Th2 and Proinflammatory Cytokines Expression in the BALF OVA/alum sensitized mice were treated with anti-CD48, anti-CD2 or anti-2B4 mAbs or control antibodies (Rat IgG, Hamster IgG) on day 23 and days 24 and 27 one hour before allergen challenge (250 μg per mice). Twenty four hours after the last allergen challenge BALF was performed and the cells were stained for differential cell identification. CCR3$^+$/VLA4$^+$/CD3$^-$/SSC$^{high}$ cells were gated and considered as eosinophils (A). Assessment of IL-4, IL-5, IL-13, TNF-α, eotaxin-1 (B-F respectively) in the BALF was detected by ELISA according to the manufacturers' instructions. Data are represented as mean±SD of $n=3$ (4-6 mice/group/n). Anti-CD48, anti-CD2 or anti-CD48 antibodies were administered systemically to naïve Balb/c mice (250 μg/mouse). After 24 hrs the mice were sacrificed and differential cell population in the spleen and peripheral blood were monitored. A histogram plot analysis of spleen cell populations is shown (G). Data are expressed as mean±SD, $n=3$.

FIG. 11A-D: Neutralization of CD48 attenuates lung inflammation Mice were sensitized, challenged and treated as described. The lung tissue was fixed, paraffin embedded and stained with H&E for assessment of inflammation. Representative photomicrographs (magnification: ×40) of airway inflammation in the different treatment groups (A). Quantitative analysis of alveolar space (B), peribronchial inflammation (C) and lung perivascular (D) is presented. Data are the mean±SD of $n=3$ (4-6 mice/group/n).

Figure 12A:
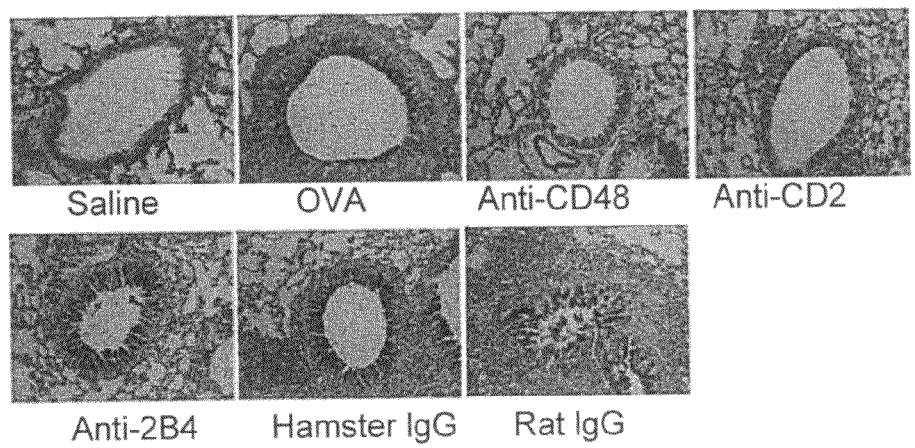
Figure 12B:
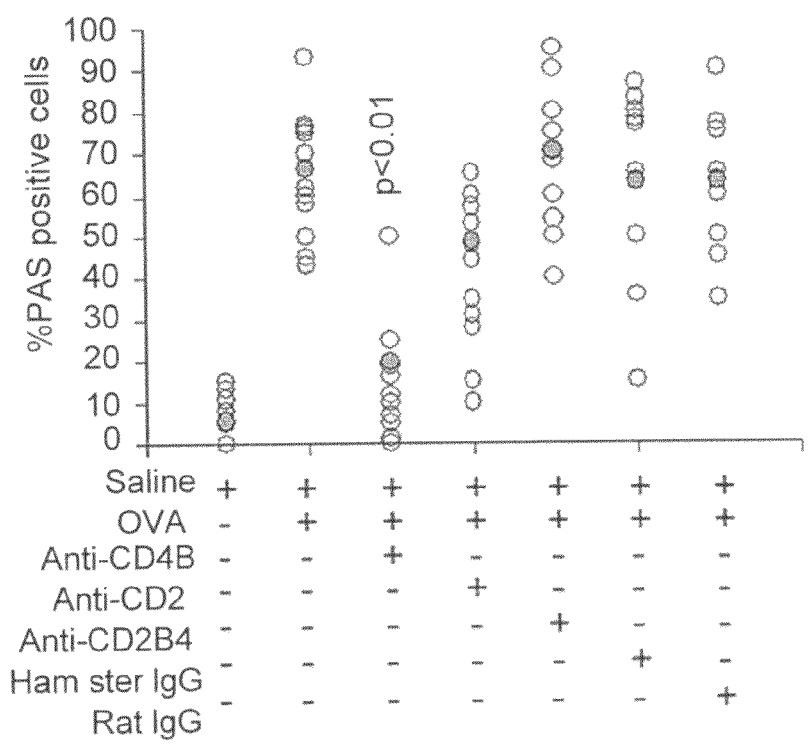
Figure 12C:
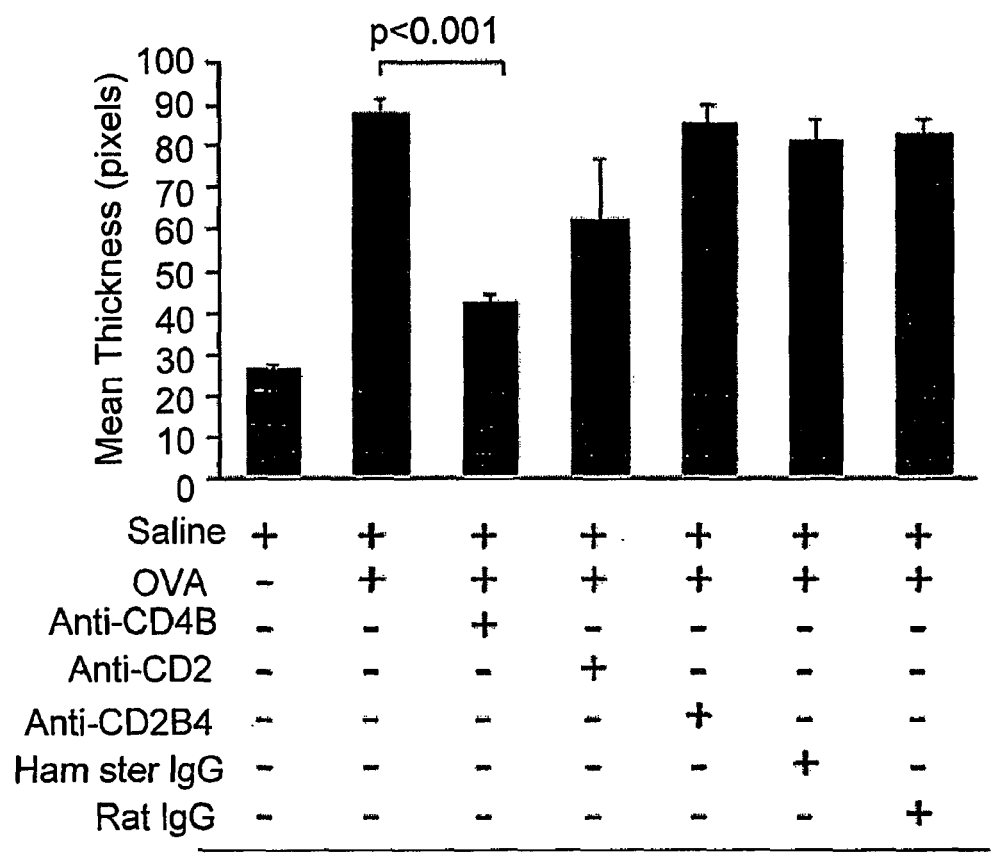

FIG. 12A-C: Neutralization of CD48 Attenuates Goblet Cell Hyperplasia, Mucus Production and Smooth Muscle Thickening in the Lung.

Mice were sensitized, challenged and treated as described. The lung tissue was fixed, paraffin-embedded and stained with PAS for assessment of goblet cell hyperplasia and mucus production. A representative photomicrograph (magnification: ×40) of airway PAS staining in the different mice treatments (A). Quantitative analysis of PAS$^+$ cells in the bronchial epithelium (B). Peribronchial smooth muscle thickening was analyzed (C). Open circles represent the mean peribronchial smooth muscle thickness in pixels of three mid sized bronchioles per mouse. Data are the mean±SD of $n=3$ (4-6 mice/group/n).

DETAILED DESCRIPTION OF THE INVENTION

The present study is the first demonstration (both in humans and mice) that CD48 is expressed in eosinophils and its expression is directly correlated with the triggering of the asthmatic response, as detailed below. Furthermore, it is also the first report implicating CD48 in allergy, and the allergic response.

Thus, in a first aspect, the present invention provides a method of treating an allergic condition, specifically, allergic airway inflammation such as asthma or nasal polyposis, atopic dermatitis, conjunctivitis and intestinal allergy. The method of the invention comprises administering a therapeutically effective amount of an anti-CD48 agent that blocks CD48 stimulatory pathway, to a subject in need of said treatment.

In one specific embodiment, said anti-CD48 agent is an anti-CD48 antibody.

In a more particular aspect, the present invention provides a method of inhibiting the activity and/or expression of CD48 in cells of a subject suffering from an allergic condition, wherein said method comprises in vivo contacting said cells with an effective amount of an anti-CD48 agent.

It should be appreciated that the invention further encompasses ex vivo contacting said cells with the anti-CD48 agent.

Thus, as mentioned above, the present invention relates to a method for the treatment of allergic conditions such as asthma, atopic dermatitis, conjunctivitis, intestinal allergy, and nasal polyposis, through abrogating, inhibiting or decreasing CD48 expression, or through eliminating, reducing or neutralizing CD48 activity. Such treatment comprises administering a therapeutically effective amount of an anti-CD48 agent to a subject in need.

As used herein, the term "anti-CD48 agent" or "an agent that blocks CD48 stimulatory pathway" refers to any compound, complex or composition which reduces, or even abrogates, the physiological phenomena which are caused by, or are downstream from CD48 activation. More particularly, such agent reduces or even inhibits the stimulatory signaling by other member molecules which are down-stream from the CD48 molecule, in such pathway which is involved in the allergic inflammatory condition. Said agent may be effective at various levels: firstly at the mRNA expression level, where CD48 (or any other down-stream member molecule) expression may be reduced (or inhibited) by inhibiting its transcripts e.g. through specific antisense oligonucleotides or by various modes of interfering RNAs, such as RNAi, siRNA, microRNA and ribozyme, which more directly interfere with translation.

Antisense oligonucleotides refer to a nucleotide comprising essentially a reverse complementary sequence to a sequence of CD48 mRNA. The nucleotide is preferably an oligodeoxynucleotide, but also ribonucleotides or nucleotide analogues, or mixtures thereof, are contemplated by the invention. The antisense oligonucleotide may be modified in order to enhance the nuclease resistance thereof, to improve its membrane crossing capability, or both. The antisense oligonucleotide may be linear, or may comprise a secondary structure. It may also comprise enzymatic activity, such as ribozyme activity.

By "ribozyme" it is meant an RNA molecule which has complementarity in a target binding region to a specified gene target, for example CD48, and also has an enzymatic activity which is active to specifically cleave target RNA. Said molecule is capable of catalyzing a series of reactions including the hydrolysis of phosphodiester bonds in trans (and thus can cleave other RNA molecules) under physiological conditions. Such enzymatic nucleic acid molecules can be targeted to virtually any RNA transcript, and achieve efficient cleavage in vitro. That is, the enzymatic RNA molecule is able to intermolecularly cleave RNA and thereby inactivate a target RNA molecule. The complementary regions allow sufficient hybridization of the enzymatic RNA molecule to the target RNA and which ensures specific cleavage. One hundred percent complementarity is preferred, but complementarity as low as 50-75% may also be useful in this invention. The nucleic acids may be modified at the base, sugar, and/or phosphate groups.

The term "siRNAs" refers to short interfering RNAs. The term "RNA interference" or "RNAi" refers to the silencing or decreasing of gene expression by siRNAs. It is the process of sequence-specific, post-transcriptional sequence-specific gene silencing in animals and plants, initiated by siRNA that is homologous in its duplex region to the sequence of the gene to be silenced, particularly CD48. The expression of the gene is either completely or partially inhibited. RNAi may also inhibit the function of a CD48 RNA, and said function may be completely or partially inhibited.

By "microRNA" is meant, single-stranded RNA molecules of about 21-23 nucleotides in length thought to regulate the expression of other genes. miRNAs are encoded by genes that are transcribed from DNA but not translated into protein (non-coding RNA), instead they are processed from primary transcripts known as pri-miRNA to short stem-loop structures called pre-miRNA and finally to functional miRNA. Mature miRNA molecules are complementary to regions in one or more messenger RNA (mRNA) molecules, which they target for degradation.

Alternatively, CD48 activity may be reduced through the use of an antagonist of the receptor, a partial antagonist or an antibody that either competes with the natural agonist, blocks the activity or encourages the uptake of the CD48 molecule. The anti-CD48 agent may thus be a nucleic acid sequence, a protein, a peptide, an antibody or a small organic molecule.

Thus, as mentioned above, a preferred anti-CD48 agent is an anti-CD48 antibody, but other agents may be effective as well, such as CD48-specific siRNA, RNAi, microRNA and Ribozyme. Other CD48 inhibitors and/or antagonists include anti-CD48 specific antibody fragments (F(ab')2 or Fab'), single chain Fv, and Fc-fusion protein of CD48 ligands, e.g. Fc fusion proteins of 2B4 or CD2.

The anti-CD48 antibody used in the method of treatment may be of polyclonal or monoclonal origin. A monoclonal antibody may be improved, through a humanization process, to overcome incompatibility problems. Rapid new strategies have been developed recently for antibody humanization which may be applied for such antibody. These technologies maintain the affinity, and retain the antigen and epitope specificity of the original antibody [Rader, C., et al. (1998) *Proc. Natl. Acad. Sci. USA*. 95: 8910-8915; Mateo, C. et al. (1997) *Immunothechnology* 3: 71-81]. A "humanized" antibody, in which, for example animal (say murine) variable regions are fused to human constant regions, or in which murine complementarity-determining regions are grafted onto a human antibody. Unlike, for example, animal-derived antibodies, "humanized" antibodies often do not undergo an undesirable reaction with the immune system of the subject.

Thus, as used herein, the term "humanized" and its derivatives refers to an antibody which includes any percent above zero and up to 100% of human antibody material, in an amount and composition sufficient to render such an antibody less likely to be immunogenic when administered to a human being. It is being understood that the term "humanized" reads also on human derived antibodies or on antibodies derived from non-human cells genetically engineered to include functional parts of the human immune system coding genes, which therefore produce antibodies which are fully human.

As referred to herein, CD48 expression may be understood as the presence of CD48 protein or mRNA in the cells of interest, particularly leucocytes, more particularly eosinophils. It should be appreciated that the invention further encompasses the presence of CD48 in any body fluid sample and in any immune-system cell (particularly the Th2 associated cells).

The expression of CD48 was evaluated on human peripheral blood eosinophil after incubation with various cytokines and chemokines, among them IL-3, IL-5 and GM-CSF, which are eosinophil survival cytokines and chief regulators of eosinophil functions, including priming and activation [Giembycz, M. A. and Lindsay, M. A. (1999) *Pharmacol. Rev.* 51: 213-340]. These cytokines share a βC-chain that is responsible for activating their signaling pathways and consequent effects.

As per the results presented herein, elevated levels of CD48 expression, as compared to a negative control, provide a positive diagnosis of an allergic condition such as asthma, allergy (atopic dermatitis, conjunctivitis and intestinal allergy), or nasal polyposis, whereas low (or absent) levels of CD48 expression may be interpreted as a negative diagnosis of the same.

Thus, a further aspect of the present invention concerns a method for the diagnosis of an allergic condition and particularly of asthma and related conditions, said method comprising obtaining a biological sample from the examined subject and determining the level of expression of CD48 in the sample. Elevated expression of CD48, in comparison with negative control, indicates the presence of asthma or an asthma-related condition. Preferably, the biological sample may be a body fluid sample such as leucocyte-containing body fluid, blood, lymph, milk, urine, faeces, semen, appendix, spleen, extractstears, sputum, nasal, mucus, amniotic fluid, bronchoalveolar lavage, pleuric fluid, peritoneal fluid and tonsillar tissue extractstears, more preferably, a leucocyte-containing body fluid. It should be noted that the leucocyte-containing body fluid may be any body fluid, for example, blood, lymph, milk, urine, faeces, semen, appendix, spleen, extractstears, sputum, nasal, mucus, amniotic fluid, bronchoalveolar lavage, pleuric fluid, peritoneal fluid and tonsillar tissue extractstears.

Said diagnostic method of the invention may be applied at two levels. In one embodiment, CD48 is detected at the protein level, in which case said method comprises contacting a biological sample with a CD48 binding agent and measuring the level of binding of said agent to said CD48 protein, whereby elevated binding of CD48, in comparison with a negative control, indicates the presence of said allergic condition. Preferably, said CD48 binding agent is an anti-CD48 antibody.

Detection of CD48 at the protein level may be effected through various means, including the detection of CD48 in intact cells, as in e.g. FACS analysis, ELISA Spot Assay or immunohistochemistry, or through any methodology which involves cell lysis and protein detection, such as e.g. Western Blot, ELISA, RIA, etc. All these methodologies are well known to the man skilled in the art, and have been described, e.g., in Current Protocols in Immunology, Coligan et al. (eds), John Wiley & Sons. Inc., New York, N.Y., 1999.

It should be noted that the term "antibody" as used herein throughout this specification is meant to include intact molecules as well as fragments thereof, such as, for example, Fab and F(ab')$_2$, which are capable of binding antigen, in this case the CD48 molecule (or protein). Such antibody fragments are within the scope of the present invention and may be used for the kits and the treatment and diagnostic methods disclosed herein for intact antibody molecules, to the extent where said fragments have the same biological activity, e.g. inhibition of CD48 function/expression, or recognition of the CD48 protein, as the intact antibody. Such fragments are typically produced by proteolytic cleavage, using enzymes such as papain (to produce Fab fragments) or pepsin (to produce F(ab')$_2$ fragments).

Said antibody may be of polyclonal or monoclonal antibody. Methods of preparing polyclonal and monoclonal antibodies are well known to the man skilled in the art.

The biological sample used by the invention may be treated with a solid phase support or carrier such as nitrocellulose, or other solid support or carrier which is capable of immobilizing cells, cell particles or soluble proteins. The support or carrier may then be washed with suitable buffers followed by treatment with a detectably labeled antibody in accordance with the present invention, as noted above. The solid phase support or carrier may then be washed with the buffer a second time to remove unbound antibody. The amount of bound label on said solid support or carrier may then be detected by conventional means.

By "solid phase support", "solid phase carrier", "solid support", "solid carrier", "support" or "carrier" is intended any support or carrier capable of binding antigen (CD48) or antibodies against CD48. Well-known supports or carriers, include glass, polystyrene, polypropylene, polyethylene, dextran, nylon amylases, natural and modified celluloses, polyacrylamides, and magnetite. The nature of the carrier can be either soluble to some extent or insoluble for the purposes of the present invention. The support material may have virtually any possible structural configuration so long as the coupled molecule is capable of binding to an antigen or antibody. Thus, the support or carrier configuration may be spherical, as in a bead, cylindrical, as in the inside surface of a test tube, or the external surface of a rod. Alternatively, the surface may be flat such as a sheet, test strip, etc. Preferred supports or carriers include polystyrene beads. Those skilled in the art will know many other suitable carriers for binding antibody specific for CD48 or the CD48 antigen, or will be able to ascertain the same by use of routine experimentation.

The binding activity of a given lot of antibody, of the invention as noted above, may be determined according to well known methods. Those skilled in the art will be able to determine operative and optimal assay conditions for each determination by employing routine experimentation.

Other such steps as washing, stirring, shaking, filtering and the like may be added to the assays as is customary or necessary for the particular situation.

One of the ways in which an anti-CD48 antibody in accordance with the present invention can be detectably labeled is by linking the same to an enzyme and used in an enzyme immunoassay (EIA). This enzyme, in turn, when later exposed to an appropriate substrate, will react with the substrate in such a manner as to produce a chemical moiety which can be detected, for example, by spectrophotometric, fluorometric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may be accomplished using any of a variety of other immunoassays. For example, by radioactive labeling the antibodies or antibody fragments, it is possible to detect receptor tyrosine phosphatase (R-PTPase) through the use of a radioimmunoassay (RIA). A good description of RIA may be found in Laboratory Techniques and Biochemistry in Molecular Biology, by Work, T. S. et al., North Holland Publishing Company, NY (1978) with particular reference to the chapter entitled "An Introduction to Radioimmune Assay and Related Techniques" by Chard, T., incorporated by reference herein. The radioactive isotope can be detected by such means as the use of a γ counter or a scintillation counter or by autoradiography.

It is also possible to label an antibody in accordance with the present invention with a fluorescent compound. When the fluorescently labeled antibody is exposed to light of the proper wavelength, its presence can be then detected due to fluorescence. Among the most commonly used fluorescent labeling compounds are fluorescein isothiocyanate, rhodamine, phycoerythrine, pycocyanin, allophycocyanin, o-phthaldehyde and fluorescamine.

The antibody can also be detectably labeled using fluorescence emitting metals such as $^{152}E$, or others of the lanthanide series. These metals can be attached to the antibody using such metal chelating groups as diethylenetriamine pentaacetic acid (ETPA).

The antibody can also be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the anti-CD48 antibody used by the diagnostic method of the invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

An antibody molecule of the present invention may be adapted for utilization in an immunometric assay, also known as a "two-site" or "sandwich" assay. In a typical immunometric assay, a quantity of unlabeled antibody (or fragment of antibody) is bound to a solid support or carrier and a quantity of detectably labeled soluble antibody is added to permit detection and/or quantitation of the ternary complex formed between solid-phase antibody, antigen, and labeled antibody.

Typical, and preferred, immunometric assays include "forward" assays in which the antibody bound to the solid phase is first contacted with the sample being tested to extract the antigen from the sample by formation of a binary solid phase antibody-antigen complex. After a suitable incubation period, the solid support or carrier is washed to remove the residue of the fluid sample, including unreacted antigen, if any, and then contacted with the solution containing an unknown quantity of labeled antibody (which functions as a "reporter molecule"). After a second incubation period to permit the labeled antibody to complex with the antigen bound to the solid support or carrier through the unlabeled antibody, the solid support or carrier is washed a second time to remove the unreacted labeled antibody.

In another type of "sandwich" assay, which may also be useful for detection of CD48 according to the diagnostic method of the present invention, the so-called "simultaneous" and "reverse" assays are used. A simultaneous assay involves a single incubation step as the antibody bound to the solid support or carrier and labeled antibody are both added to the sample being tested at the same time. After the incubation is completed, the solid support or carrier is washed to remove the residue of fluid sample and uncomplexed labeled antibody. The presence of labeled antibody associated with the solid support or carrier is then determined as it would be in a conventional "forward" sandwich assay.

In the "reverse" assay, stepwise addition first of a solution of labeled antibody to the fluid sample followed by the addition of unlabeled antibody bound to a solid support or carrier after a suitable incubation period is utilized. After a second incubation, the solid phase is washed in conventional fashion to free it of the residue of the sample being tested and the solution of unreacted labeled antibody. The determination of labeled antibody associated with a solid support or carrier is then determined as in the "simultaneous" and "forward" assays.

In another embodiment, said diagnostic method is effected at the mRNA level, in which case said determination comprises measuring the level of CD48 mRNA expression by appropriate means, whereby elevated levels of CD48 mRNA, in comparison with a negative control, indicates the presence of an allergic condition, specifically, asthma.

Appropriate means for measuring mRNA levels include applying the methods of RT-PCR, PCR, Nucleic acid based ELISA and hybridization with a labeled probe, e.g. in Northern blot, or in situ hybridization. These are well known methods which are familiar to the man skilled in the art of molecular biology.

Nucleic acid based ELISA may be performed by coating ELISA plates with antisense nucleic acid sequence derived from CD48, incubating tagged or labeled RT-PCR products obtained from the examined sample with the plates and quantitating the bound nucleic acid sequence. Tag's suitable for such purpose may be for example avidin/biotin, GFP, myc, FLAG and the like.

In one further specific embodiment of the diagnostic method of the invention, when effected at the mRNA level, said determination comprises providing primers for specific amplification of CD48 transcripts, together with nucleotides and amplification reagents, providing conditions for allowing CD48 amplification, whereby elevated levels of CD48 amplification products, in comparison with a negative control, indicates the presence of at least one of asthma, allergy or an asthma- or allergy-related condition.

Thus, as used herein "RT-PCR" refers to a process of reverse transcription of mRNA into cDNA which is subsequently subjected to PCR reaction. PCR (Polymerase Chain Reaction) involves amplifying one or more specific nucleic acid sequences by repeated rounds of synthesis and denaturing under appropriate conditions.

PCR requires two primers that are capable of hybridization with a single-strand of a double-stranded target nucleic acid sequence which is to be amplified under appropriate hybridization conditions. In PCR, this double-stranded target sequence is denatured and one primer is annealed to each single-strand of the denatured target. The primers anneal to the target nucleic acid at sites removed (downstream or upstream) from one another and in orientations such that the extension product of one primer, when separated from its complement, can hybridize to the extension product generated from the other primer and target strand. Once a given primer hybridizes to the target sequence, the primer is extended by the action of a DNA polymerase. DNA polymerase which is heat stable is generally utilized so that new polymerase need not be added after each denaturation step. Such thermostable DNA polymerase is known to one of ordinary skill in the art, e.g. Taq polymerase. The extension product is then denatured from the target sequence, and the process is repeated.

In a specifically preferred embodiment, the primer extension or PCR product may be un-labeled. In this case, the gel-banding pattern of the resulting fragments may be visualized by ethidium bromide (EtBr), or by silver staining. Alternatively, the primer extension or PCR product may be body-labeled, by using labeled nucleotide during the PCR reaction. The term "label" as used herein refers to any atom or molecule which can be used to provide a detectable (preferably quantifiable) signal, and which can be attached to a nucleic acid or protein. Labels may provide signals detectable by fluorescence, radioactivity, colorimetry, gravimetry, X-ray diffraction or absorption, magnetism, enzymatic activity, and the like.

As used herein, the term "nucleic acid" refers to polymer of nucleotides, which may be either single- or double-stranded, which is a polynucleotide such as deoxyribonucleic acid (DNA), and, where appropriate, ribonucleic acid (RNA). The terms should also be understood to include, as equivalents, analogs of either RNA or DNA made from nucleotide analogs, and, as applicable to the embodiment being described, single-stranded (such as sense or antisense) and double-stranded polynucleotides. The term DNA used herein also encompasses cDNA, i.e. complementary or copy DNA produced from an RNA template by the action of reverse transcriptase (RNA-dependent DNA polymerase).

It is important to note that the results obtained through the herein described diagnostic methods are always compared to a reference value, obtained e.g. from a negative control, which assists the medical practitioner to arrive at the correct diagnosis, positive or negative.

The inventors tested the involvement of key molecules which are hallmarks of mechanisms in the allergic asthmatic response such as e.g. STAT6, IL-4, IL-13, IL-5 and eotaxin-1. These mechanisms have been previously showed to regulate several genes that were present on the "asthma genome signature" such as TFF2, ADAM8, eotaxin-1 and arginase. Nevertheless, numerous genes related to allergic inflammation are STAT6-independent, including CXCL10, CXCL12 and Clq [Fulkerson, P. C. et al. (2004) *J. Immunol.* 173: 7565-74]. Mechanistic analysis of these pathways revealed that CD48 was upregulated in the absence of STAT6, IL-4 and IL-13. Interestingly, CD48 expression was found to be spontaneously upregulated in inducible IL-13 transgenic mice.

More particularly, to determine whether IL-3 physiologically upregulates CD48 in allergic disorders, CD48 expression on eosinophils was evaluated in a murine experimental asthma and allergic peritonitis. The data obtained from the model presented herein demonstrate that CD48 expression increased in a time-dependent fashion after allergen challenge. IL-3 neutralization in OVA-challenged mice reduced eosinophil CD48 expression, but not to the baseline level that is observed in saline-treated mice. Thus, although IL-3 is the only identified cytokine that up-regulates eosinophil CD48 expression, it is unlikely to be the only factor responsible for this phenomenon in vivo. It is possible that IL-3 and IL-4 act in concert to influence CD48 expression on various cell types. Alternatively, higher doses of anti-IL-3 may be required for a more dramatic effect.

Cross-linking of CD48 on human eosinophils triggered EPO but not cytokine release even in the presence of IL-3. It is possible that IL-3 potentiates the responses elicited by CD48. In support of this hypothesis, it is the inventors' observation that IL-3 enhances the ability of eosinophils to internalize *E. coli* via CD48 (Munitz et al., unpublished observations). Furthermore, IL-3 has been shown to prime eosinophils and augment eosinophil-LTC4 generation in response to calcium ionophore and enhance cytotoxicity towards antibody-coated helminthes [Rothenberg, M. E. et al. (1988) *J. Clin. Invest.* 81: 1986-1992]. Therefore, it is possible that CD48 together with IL-3 regulates the release of specific mediators that are beneficial to the host in helminth and bacterial infections (i.e. innate mechanisms) but unfavorable in allergic settings (i.e. adaptive mechanisms).

Thus, the inventors may hypothesize that compensatory mechanisms (yet to be defined) present in the lungs of allergen-challenged mice can upregulate CD48 in the absence of one single pathway. It should be noted that the possibility that CD48 is upregulated in the lungs of OVA-challenged mice due to local inflammation and recruitment of CD48-expressing cells, cannot be ruled out. Yet, upregulation of CD48 was unchanged in STAT-6, IL-4, IL-13 and eotaxin-1/IL-5 deficient mice, which fail to develop an eosinophil infiltrate (data not shown). Thus, upon allergen challenge lung expression of CD48 remains unaltered. This could result from compensatory mechanisms that recruit other CD48$^+$ cell types such as lymphocytes and neutrophils rather than eosinophils.

It is likely that CD48 signaling cascade contributes to eosinophil activation and degranulation in asthma. As complex networks of activating and inhibitory signals govern the responses coordinated by eosinophils, increased CD48 expression might shift the resting threshold of eosinophils toward activation.

While the role and pathways regulating NKT cell functions in allergic inflammations such as asthma are still to be determined, the results of the present invention suggests that 2B4 does not play a significant role in their activation in allergic settings.

CD48 can induce signal transduction as it binds Lck, Fyn and G proteins [Patel, V. P. et al. (2001) *J. Immunol.* 166: 754-64; Stefanova, I, et al. (1991) *Science* 254: 1016-9)]. Cross-linking of CD48 on purified tonsillar B cells significantly increased CD40-mediated activation [Klyushnenkova, E. N. et al. (1996) *Cell Immunol.* 174: 90-8], and cross-linking CD48 in combination with IL-4 and/or IL-10 is able to induce B cell aggregation, proliferation and IgG secretion. Therefore, the anti-CD48 agent used by the method of the invention may target other down-stream member molecules of the CD48 stimulatory pathway, such as Lck, Fyn and G proteins.

More particularly, CD48 is upregulated on the single cell level by at least two mediators that are expressed in the asthmatic milieu: IL-3 and IL-4. The abundance of pathways that regulate CD48 expression in vivo highlights CD48 importance. This led the inventors to investigate the CD48-CD2-2B4 axis in allergic eosinophilic airway inflammation pathogenesis. To examine this, the inventors administered anti-CD48, anti-CD2 and anti-2B4 neutralizing antibodies prior to allergen challenge. Strikingly, neutralization of CD48 significantly reduced eosinophilic inflammation and cytokine expression (i.e Th2 cytokines; IL-5, IL-4 and IL-13, proinflammatory cytokines; TNF-α, chemokines; eotaxin-2) in the BALF. Moreover, it abrogated lung inflammation (alveolar space, perivascular and peribronchial) airway smooth muscle thickening, epithelial shedding, goblet cell hyperplasia and mucus production. Neutralization of CD2 caused a ~40-50% reduction in these inflammatory parameters while anti-2B4 treated mice displayed no significant effect.

Several mechanisms could account for the anti-inflammatory effects of blocking CD48. CD48 deficient mice show considerable defects in CD4$^+$ T cell activation. The inhibitory effect of anti-CD48 treatment in our settings is likely to be only partially dependent on T cell co-stimulation via CD2, since anti-CD2 treated mice displayed a mild reduction of the disease parameters in comparison to anti-CD48 mAb treated mice. Supporting this finding is the observation that CD2 deficient mice do not display the same effects observed in CD48 deficient mice. This suggests a broader and more substantial role for CD48 in the immune system than recognized. Several line of evidence supports a broad immunological role for CD48.

The demonstration that CD48 is up-regulated in experimental asthma indicates the role of this molecule in human disease as well. Interestingly, CD48 was up-regulated both in human peripheral blood eosinophils and in human nasal polyp eosinophils of atopic asthmatics vs. normal controls. The latter finding is of great consideration since the most prevalent disease associated with nasal polyposis is bronchial asthma.

The present results clearly define a novel pathway that is critically involved in the orchestration and regulation of experimental and human asthma. Therefore, CD48 is herein presented as a new target for future therapeutic and diagnostic approaches.

As referred to herein, the term "asthma" or "asthmatic condition" refers to a medical condition characterized by recurrent attacks of paroxysmal dyspnea, with airway inflammation and wheezing due to spasmodic contraction of the bronchi. In other words, asthma is an inflammatory condition of the bronchial airways, characterized by airflow obstruction and bronchial hyper-responsiveness, resulting in increased mucus production, mucosal swelling and muscle contraction. These changes produce airway obstruction, chest tightness, coughing and wheezing. When severe, this can cause severe shortness of breath and low blood oxygen.

The asthmatic condition has various etiologies, including allergic manifestations in sensitized individuals ("allergic asthma"), asthma provoked by factors such as vigorous exercise, irritant particles, viral respiratory infections and/or psychological stress ("bronchial asthma" or "spasmodic asthma"), amongst others.

Allergy may be defined as a reaction to foreign substances (allergens) by the immune system. Examples of allergens include pollens, dust mite, molds, dander, and certain foods.

The most common allergic conditions include hay fever (allergic rhinitis), asthma, allergic eyes (allergic conjunctivitis), allergic eczema, hives (urticaria), and allergic shock (also called anaphylaxis and anaphylactic shock).

More specifically, "conjunctivitis" is an inflammation of the conjunctiva (the outermost layer of the eye and the inner surface of the eyelids), most commonly due to an allergic reaction or an infection (usually bacterial or viral).

"Atopic dermatitis" (AD) is a chronic, highly pruritic, eczematous skin disease that follows patients from early childhood into puberty and sometimes adulthood. Also referred to as eczematous dermatitis, the disease often has a remitting/flaring course, which may be exacerbated by social, environmental, and biological triggers.

For the method of treatment provided in the present invention, said therapeutic effective amount, or dosage, is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. In general, dosage is calculated according to body weight, and may be given once or more daily, weekly, monthly or yearly, or even once every 2 to 20 years. Persons of ordinary skill in the art can easily estimate repetition rates for dosing based on measured residence times and concentrations of the anti-CD48 agent in bodily fluids or tissues. Following successful treatment, it may be desirable to have the patient undergo maintenance therapy to prevent the recurrence of the disease state, wherein the anti-CD48 agent is administered in maintenance doses, once or more daily.

Various methods of administration may be used for delivering the anti-CD48 agent to a subject in need. It should be emphasized that a localized administration of the anti-CD48 agent is specifically preferred. Said agent may be delivered via intravenous (i.v.), intramuscular (i.m.), intraperitoneal (i.p.) injections, orally (in liquid form or prepared as dosage unit forms like capsules, pills, lozenges, etc.). Alternatively and preferably, the anti-CD48 agent may also be delivered in a local manner, via transdermal delivery using patches, ointment or cream. Other routes of administration are intranasal, intradermal, sub-lingual, and intrathecal, although systemic delivery may be also used. Possible delivery devices include aerosol (inhalation), liposomal carriers, drops, ready-to-use syringes, pills and capsules, amongst others.

Taken together the present results suggest that CD48 may serve as a multifaceted molecule that regulates several eosinophil effector functions in disease settings. For example, elevated levels of CD48 on eosinophils and basophils correlated with increased infiltration of these cells to the lung, BALF and spleen. In addition, CD48 has been reported to function as an adhesion molecule [Yokoyama, S. D. et al. (1991) *J. Immunol.* 146: 2192-2200], and it can bind directly to heparin sulfate on the surface of epithelial cells [Ianelli, C. J. et al. (1998) *J. Biol. Chem.* 273: 23367-23375]. Consequently, CD48 may influence homing, transmigration, and tissue retention of eosinophils in allergic settings.

Therefore, the present invention also provides the use of an anti-CD48 agent as a preventive vehicle for allergic conditions. Given the present findings that CD48 is one of the molecules at the top of the signaling cascade involving the allergic response (which triggers the asthma attack), inhibiting CD48 function/expression is a way of preventing the asthmatic or allergic condition to take place. Such a drug is certainly a leap forward in asthma and allergy drug development, in view, that asthmatic and/or allergic patients are usually treated with drugs that ease the symptoms, but are not spared from the agony of the attack. A preventive drug is hence much in demand for this target population.

By "patient" or "subject in need" it is meant any mammal who may be affected by the above-mentioned conditions, and to whom the treatment and diagnosis methods herein described is desired, including human, bovine, equine, canine, murine and feline subjects. Preferably said patient is a human.

In conclusion, the present results support the idea that CD48 has an important role in eosinophil activation in a variety of allergic conditions not previously described.

Lastly, the present invention also provides a kit for the diagnosis of an allergic condition, specifically, asthma and related conditions, said kit comprising as follows:
  (a) an agent for determining the presence of an analyte of interest, wherein said analyte is selected from the group consisting of: CD48 protein and CD48 mRNA;

(b) calibration means; and
optionally a manual of instructions of how to perform the diagnostic test.

Where the analyte is CD48 protein, said agent is an anti-CD48 antibody. Said antibody may be conjugated to a detectable label or not. In case said antibody is not conjugated to a detectable label, a second antibody is also supplied by the kit of the invention, wherein said second antibody is conjugated to a detectable label, it is produced in a different species from the first antibody, and it is capable of detecting the first antibody.

Evidently, where the analyte is CD48 mRNA, said agent may be a CD48-specific probe, said probe being a oligonucleotide sequence complementary and specific to the CD48 mRNA sequence, labeled by any suitable means, e.g. immunofluorescence labeling, luminescence, radioisotopes, etc.

Alternatively, the detection of CD48 mRNA may be effectuated through amplification of said specific mRNA, in PCR or RT-PCR reactions, and in which case said agent is a CD48-specific primer (typically specific complementary oligonucleotides).

The detection per se may be performed e.g. using FACS analysis, wherein the sample is analyzed by FACS using the appropriate parameters and comparing to a negative control. Alternatively, the cells obtained from the collected sample may be fixed onto a slide, and CD48 expression detected via anti-CD48 antibodies or labeled probes (in situ detection). Yet another detection method which may be utilized involves protein or RNA extraction and analysis, via e.g. Western blot, ELISA, Northern blot or PCR. Any one of these alternatives is specified in the manual of instructions accompanying the kit, accordingly.

As mentioned herein, calibration means may be a sample of a negative control in order to give a yes/no binary answer. The calibration may also comprise a full calibration curve in order to give a quantitative answer as regards the severity of the allergic reaction, or of the asthmatic condition.

In another embodiment, said kit may optionally further comprise at least one of the following components: means for obtaining a blood sample, means for isolating leucocytes from the blood sample, and means for detecting the anti-CD48 antibody or CD48-specific probe.

The invention further provides a pharmaceutical composition for the treatment of an allergic condition comprising as an active ingredient a therapeutically effective amount of an anti-CD48 agent and optionally further comprising pharmaceutically acceptable carrier, diluent, excipients and/or additive.

The present invention is defined by the claims, the contents of which are to be read as included within the disclosure of the specification, and will now be described by way of example with reference to the accompanying Figures.

Disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following Examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Experimental Procedures

A number of methods of the art of molecular biology are not detailed herein, as they are well known to the person of skill in the art. Such methods include site-directed mutagenesis, PCR cloning, expression of cDNAs, analysis of recombinant proteins or peptides, transformation of bacterial and yeast cells, transfection of mammalian cells, and the like. Textbooks describing such methods are e.g., Sambrook et al., Molecular Cloning A Laboratory Manual, Cold Spring Harbor Laboratory; ISBN: 0879693096, 1989, Current Protocols in Molecular Biology, by F. M. Ausubel, ISBN: 047150338X, John Wiley & Sons, Inc. 1988, and Short Protocols in Molecular Biology, by F. M. Ausubel et al. (eds.) 3rd ed. John Wiley & Sons; ISBN: 0471137812, 1995. These publications are incorporated herein in their entirety by reference. Furthermore, a number of immunological techniques are not in each instance described herein in detail, as they are well known to the person of skill in the art. See e.g., Current Protocols in Immunology, Coligan et al. (eds), John Wiley & Sons. Inc., New York, N.Y., 1999.

Reagents and Chemicals:

All chemicals used in this study were purchased from Sigma (Rehovot, Israel) and were of the best available grade.

Antibodies

FITC conjugated anti-CCR3 was obtained from R&D Systems (Minneapolis, Minn.). Anti-CD3-APC, anti-VLA2-PE (DX5), anti-CD4-PE-Cy5, anti-rat-PE, anti-rat-FITC, streptavidin-PE and streptavidin-Cy5 were all purchased from eBioscience, (San Diego, Calif.). Anti-B220-APC, anti-CD2 and anti-CD48-PE were obtained from Biolegend (San Diego, Calif.). Anti-2B4 mAb (a kind gift of Dr. Vinay Kumar, University of Chicago) and anti-CD2 were conjugated to biotin using a standard protocol.

Mice:

Balb/c mice were obtained from the National Cancer Institute (Frederick, Md.) or Harlan laboratories (Israel) and housed under specific pathogen-free conditions. Mice deficient in STAT6 or IL-4Rα in the Balb/c background were obtained from Jackson Laboratories (Bar Harbor, Me.). IL-13-deficient mice and mice deficient in both IL-4 and IL-13 were kindly provided by Dr. Andrew McKenzie. Generation of eotaxin-deficient IL-5-transgenic mice was previously described [Mishra, A. et al. (1999) *J. Clin. Invest.* 103 (12):1719-27]. Mice carrying the tetracycline inducible IL-13 transgene under the regulation of the Clara cell 10 (CC10) lung promoter have been previously described [Horejsi, V. et al. (1999) *Immunol. Today* 20: 356-361].

Experimental Asthma:

BALB/c female mice (7-8 weeks old) were obtained from Harlan Laboratories (Israel) and housed under specific pathogen-free conditions. Mice were sensitized by i.p. injection with 100 μg of OVA adsorbed onto 1 mg of aluminum hydroxide in 250 µl of saline on days 0 and 14. On days 24 and 27, the mice were lightly anesthetized with inhaled isofluorane and challenged intranasally with 50 µg of OVA or saline. The allergen challenge was performed by applying 50 µl of the same to the nostrils using a micropipette with the mouse held in a supine position. After instillation, the mice were held upright until alert. Mice were sacrificed by isofluorane inhalation at the indicated time points (0-24 hrs) following allergen challenge and BALF was performed for differential cell counts [Van Rijt, L. S. et al. (2004) *J. Immunol. Meth.* 288: 111-121]. In addition, lungs were excised, digested as described [Southam, D. S. et al. (2005) *J. Allergy Clin. Immunol.* 115: 95-102], and differential cell count performed.

In neutralization experiments, anti-IL-3 (clone 8F8) (2 mg/mouse in 300 µl saline), anti-CD48, anti-CD2 (Biolegend, San Diego, Calif.), anti-2B4, or appropriate isotype matched controls (Hamster IgG and Rat IgG) were administered i.p on day 23 (24 hrs prior to allergen challenge) and on days 24 and 27 one hour prior to allergen challenge (250 µg/mouse in 300 µl saline). These concentrations were chosen because they had been previously shown to have a neutralizing effect in vivo. Mice were sacrificed 18 hrs after the last allergen challenge. BALF was performed for differential cell counts and eosinophils were assessed for CD48 expression. In addition, lungs were excised, fixed in 4% paraformaldehyde, paraffin embedded and stained by H&E (hematoxylin/eosin). Calculation of total lung inflammation was performed by assessing alveolar space and perivascular and peribronchial infiltrate using the following key: 0—no inflammation, 1—light inflammation, 2—moderate inflammation, and 3—severe inflammation.

Experimental Allergic Peritonitis:

BALB/c female mice (8-10 weeks old) were sensitized subcutaneously on days 0 and 7 with 100 µg of OVA adsorbed onto 1.6 mg of aluminum hydroxide in 300 µl saline. On day 11, the mice were challenged i.p. with 3 µg of OVA in 200 µl of saline and sacrificed at the indicated time points (6 hrs-48 hrs). Thereafter, the peritoneal cavity was washed with 5 ml of Tyrode's gelatin buffer for differential cell counts.

For experiments involving IL-5 transgenic mice, mice were obtained as described [Finkelman, F. D. et al. (1993) *J. Immunol.* 151: 1235-1244].

All experiments involving animals and primary animal cells were approved by the Institutional Animal Experimentation Ethics Committee of the Hadassah Ein Kerem Hospital.

IL-3 Administration

IL-3 (Peprotech, Rocky Hill, N.J.) was administered intranasally or systemically in lightly anesthetized (isofluorane) BALB/c female mice (7-8 weeks old). Briefly, recombinant murine IL-3 (2-4 µg in 50 µl saline for intranasal administration and 8-10 µg in 100 µl saline) was delivered in conjunction with anti-IL-3 mAb (4-20 µg) (IL-3C). This co-injection triggers the formation of an IL-3/anti-IL-3 mAb complex (IL-3C) that slowly releases IL-3 with an in vivo half-life of 24 hrs, as compared to a half-life of several minutes for free IL-3 [Finkelman (1993) ibid.]. The mice received IL-3C every other day for 21 days. Mice were sacrificed 24 hrs after the last administration of IL-3C. Spleen, lung and BALF cells were assessed for CD48 expression by FACS (see below).

Microarray Hybridization and Analysis:

Microarray hybridization was performed by the Affymetrix Gene Chip Core facility at Cincinnati Children's Hospital Medical Center (Cincinnati, Ohio, USA), as previously described [Bochner, B. S. (2004) *J. Allergy Clin. Immunol.* 113:3-9]. Briefly, total lung RNA was obtained using Trizol (Invitrogen, Grand Island, N.Y.) according to the manufacturers' instructions. RNA was converted to cDNA with Superscript choice for cDNA synthesis (Invitrogen, Carlsbad, Calif., USA) and subsequently converted to biotinylated cRNA with Enzo BioArray™ High Yield™ RNA Transcript labeling kit (Enzo Diagnostics, Farmingdale, N.Y.). After hybridization to the murine U74Av2 GeneChip (Affymetrix, Santa Clara, Calif., USA), the gene chips were automatically washed and stained with 10 streptavidin-phycoerythrin by using a fluidics system. The chips were scanned with a Hewlett Packard Gene Array Scanner. This analysis was performed with one mouse per chip (n>3 for each allergen challenge condition and n>2 for each saline challenge condition). From data image files, gene transcript levels were determined using algorithms in the Microarray Analysis Suite Version 4 software (Affymetrix). Differences between saline- and OVA-treated mice were also determined using the GeneSpring software (Silicon Genetics, Redwood City, Calif., USA). Data for each allergen challenge time point was normalized to the average of the saline-treated mice.

Northern Blot Analysis:

Total lung RNA (10-20 µg) was analyzed by electrophoresis in an agarose-formaldehyde gel, transferred to Gene Screen transfer membranes (NEN, Boston, Mass., USA) in 10×SSC and cross-linked by UV radiation. Sequence confirmed probes were obtained from American Type Tissue Culture Collection (ATCC, Rockville, Md., USA) and labeled with $^{32}P$ using the Klenow reaction and random priming. Blots were hybridized under standard conditions.

Human Eosinophil Purification:

Eosinophils were purified from peripheral blood of atopic asthmatics (see below) or age and sex matched normal individuals (blood eosinophil levels 5-10%) by MACS negative immunomagnetic separation as previously described [Munitz, A. et al. (2005) ibid. *J. Immunol.* 174: 110-118]. Asthmatic donors were all atopic individuals (total IgE>100 IU/ml blood) requiring intermittent $\beta_2$-agonist treatment (FEV1 values ranging from 75%.90% of normal). Non-asthmatic gender-matched controls were non-atopic and had $FEV_1$ values greater than 95% of normal.

Written informed consent was obtained from all volunteers according to the guidelines established by the Hadassah-Hebrew University Human Experimentation Helsinki Committee.

Briefly, venous blood (50-100 ml) was collected in heparinized syringes and left to sediment in 6% dextran (Amersham Biosciences, Uppsala, Sweden). Leukocytes were centrifuged on Ficoll-Hypaque (density 1.077, Amersham Biosciences, Uppsala, Sweden), for 25 min, 700 g, 22° C. Neutrophils and contaminating lymphocytes were tagged in the granulocyte-enriched pellet with micromagnetic beads bound to anti-CD16 and anti-CD3 antibodies (Miltenyi Biotech, GmbH, Bergisch Gladbach, Germany). Eosinophils were purified by passing the cell suspension through a magnetic column (MACS). They were collected at a purity of at least 98%, according to Kimura's staining, and at a viability of at least 98%, as evaluated by trypan blue staining. Eosinophil preparations were re-suspended in medium containing RPMI-1640, 200 U/ml penicillin, 200 µg/ml streptomycin and 10% v/v heat inactivated FCS (RPMI 10%)

Human Nasal Polyp Digestion:

Cells were isolated and obtained from nasal polyps of atopic asthmatic patients [Munitz, A. et al. (2005) *Blood* October 27; Epub ahead of print] or age and sex matched non-asthmatic individuals according to guidelines established by the Hadassah-Hebrew University Human Experimentation Helsinki Committee. Nasal polyps were washed twice in RPMI-2% FCS, minced to fragments of ~1 mm$^3$ and subsequently digested by incubation for 60 min at 37° C. with an enzyme cocktail containing collagenase type-I (6 mg/gram tissue), hyaluronidase (3 mg/gram tissue), and DNase (100 μg/gram tissue). The digested tissue was filtered through a 150 mesh nylon cloth. Collected cells contained >55-90% eosinophils (Kimura's staining) and had a viability of >94% (Trypan blue exclusion). Contaminating cells were usually macrophages and to a lesser extent, lymphocytes. Eosinophils in the cell suspension were identified as $SSC^{high}$ and $CCR3^+$ cells using FACS analysis.

Asthmatic donors were all atopic individuals (total IgE>100 units) requiring intermittent $\beta_2$-agonist treatment ($FEV_1$ values ranging 75%-90% of normal $FEV_1$). Non asthmatic gender-matched controls were non-atopic and had $FEV_1$ values greater than 95% of normal.

Human Eosinophil Cell Culture:

For receptor up-regulation experiments, freshly isolated human peripheral blood eosinophils were seeded in 96 plate U-shaped wells (Nunc, Roskilde, Denmark) ($2\times10^5/200$ μl) in RPMI-10%, and incubated (37° C., 5% CO2) for the indicated time points with IL-3 or with various other cytokines or chemokines (2-200 ng/ml, all purchased from Peprotech, Rocky Hill, N.J.). Thereafter, the cells were washed and CD48 expression was assessed by FACS.

For mediator release assays, 96-well plates (Nunc, Roskilde, Denmark) were pre-coated with sheep anti-mouse IgG F(ab) (25 μg/ml) in PBS, for two hours, at 37° C., 5% $CO_2$. Afterwards plates were washed three times with PBS and incubated with anti-CD48 mAb (Pharmingen, San Diego, Calif.) or an irrelevant isotype-matched control mAb (DAKO, Denmark) (1 μg/ml, 2 hrs at 37°, 5% $CO_2$) and washed three times. Freshly isolated eosinophils were seeded in these pre-coated wells (2×105/200 μl) in RPMI-10% (as described above) and incubated for 30 min-18 hrs (37° C., 5% $CO_2$). At the end of the incubation, cells were centrifuged (300 g, 5 min, 4° C.), supernatants collected, aliquoted, and stored at −80° C. until assessed for EPO (eosinophil peroxidase) activity.

Eosinophil Peroxidase (EPO) Determination;

EPO release was determined by a calorimetric assay. Briefly, eosinophil culture supernatants (50 μl) were incubated (10-15 min, 37° C., 5% $CO_2$) with a substrate solution that contained 0.1 mM O-phenylenediamine dihydrochloride in 0.05 M Tris buffer (pH 8.0), 0.1% Triton X-100 (37° C., 5% $CO_2$) and 1 mM hydrogen peroxide (Merck, Darmstadt, Germany). The reaction was stopped by the addition of 4 mM sulfuric acid (BDH, Dorset, UK) and the absorbance was determined at 492 nm in a spectrophotometer (PowerWave™ XS, Bio-Tek Instruments, Bad Friedrichshall, Germany).

Flow Cytometry:

For assessment of CD48 expression on human eosinophils, cells ($2\times10^5$) were incubated with anti-CD48 (1 μg/ml, clone 4H9, Santa Cruz, Calif., USA) a final volume of 100 μl of Hanks Balanced Salt Solution supplemented with 0.1% bovine serum albumin and 0.02% sodium azide (HBA) for 30 min on ice. Thereafter the cells were washed and goat anti-mouse FITC (1:500, Jackson, Immunoresearch Laboratories, West Grove, Pa., USA) was added. After 30 min incubation (30 min, 37° C., 5% $CO_2$), the cells were washed and analyzed on a Beckton Dickinson FACScalibur™ System (Beckton Dickinson, San Jose, Calif., USA).

Total BALF cells ($2\times10^5$) of treated mice were incubated with the aforementioned antibodies in a final volume of 100 μl of Hanks Balanced Salt Solution supplemented with 0.1% bovine serum albumin and 0.02% sodium azide for 30 min on ice. Cell staining was performed by four-color flow cytometry using anti-CD3 APC, anti-c-kit Pe-Cy5, Anti-FcεRI FITC, anti-CD4 Pe-Cy5, anti-CD48 PE (eBioscience, San Diego, Calif., USA), and anti-CCR3 FITC (R&D, Systems, Minneapolis, Minn., USA). Thereafter, differential cell populations were electronically gated and assessed for expression of CD48, CD2 or 2B4. For FACS analysis, differential cell populations were defined as follows: Eosinophils—$SSC^{high}$, $CCR3^{high}$, $CD49d^{high}$, c-$kit^{low}$, $FceRI^{low}$, $Ly49b^-$ and $CD3^-$; Neutrophils—$SSC^{high}$, $CCR3^-$ and $CD3^-$; Lymphocytes—$SSC^{low}$, $CCR3^-$ and either $CD3^+$ or $B220^+$; Monocytes/macrophages—$SSC^{high}$, $FSC^{high}$, $CCR3^-$, $CD3^-$ and $FceRI^-$; NK cells—$SSC^{low}$, $CCR3^-$, $DX5^+$ and $CD3^-$: NKT cells $SSC^{low}$, $CCR3^-$, $DX5^+$ and $CD3^+$. The different cell types were identified through their surface antigens and physical parameters (SSC vs. FSC) as previously described [Van Rijt, L. S. et al. (2004) *J. Immunol. Methods* 288: 111-12]. For each staining at least ten thousand cells were collected and data analysis was performed using CellQuest™ software (Mansfield, Mass., USA).

Mediator Assessment:

Cytokines were measured with kits purchased from the following sources: IL-5; e-bioscience (San Diego, Calif.), IL-4 and IL-13; Biolegend (San Diego, Calif.), Eotaxin-2 and TNF-α; R&D systems ((Minneapolis, Minn.). ELISA procedures were carried out according to the manufacturers' instructions. Lower detection limits for the various assays were: 7.8 pg/ml, 2 pg/ml, 16 pg/ml, 32 pg/ml and 16 pg/ml respectively. Assessment of RANTES, MCP-1 and MCP-5 was performed using the RayBio® cytokine protein Arrays (RayBiotech, Norcross, Ga., USA), according to manufacturer's instructions.

Quantification of Lung Inflammation:

Histological studies were performed as follows; the right upper lobe of saline or allergen-challenged lungs was fixed in 3.7% paraformaldehyde, embedded in paraffin, deparaffinized and stained with hematoxylin and eosin or periodic acid Schiff.

Inflammatory score: H&E stained slides were examined by two blinded observers and graded using a standard scoring method (0=normal; 1=mild; 2=intermediate; 3=severe inflammation). At least three medium sized bronchioles and blood vessels were examined per slide.

PAS staining quantification: To quantify the level of mucus expression in the airway, the number of PAS-positive and PAS-negative epithelial cells in individual bronchioles was counted. At least three medium-sized bronchioles (defined by having approximately 90.150 luminal airway epithelial cells) were counted per slide. Results are expressed as the percentage of PAS-positive cells per bronchiole, which is calculated from the number of PAS-positive epithelial cells per bronchus divided by the total number of epithelial cells of each bronchiole.

Peribronchial smooth muscle thickness quantification: To quantify the levels of peribronchial smooth muscle thickening, H&E stained slides were microphotographed and the mean pixel count of at least 10 different positions per bronchiole of each smooth muscle layer was obtained. This procedure was calculated from at least three medium-sized bronchioles per mouse.

Reagents and Chemicals:

RPMI-1640 supplemented with L-glutamine, heat-inactivated Fetal Calf Serum (FCS) and penicillin-streptomycin solutions were obtained from Biological Industries (Beit Haemek, Israel). All the chemicals used in this study were purchased from Sigma (Rehovot, Israel) and were of best available grade.

Statistical Analysis:

Statistical significance was calculated using parametric analysis (ANOVA, followed by students' t-test assuming equal variance). Values were considered significant at p<0.05.

Example 1

Figure 1A:
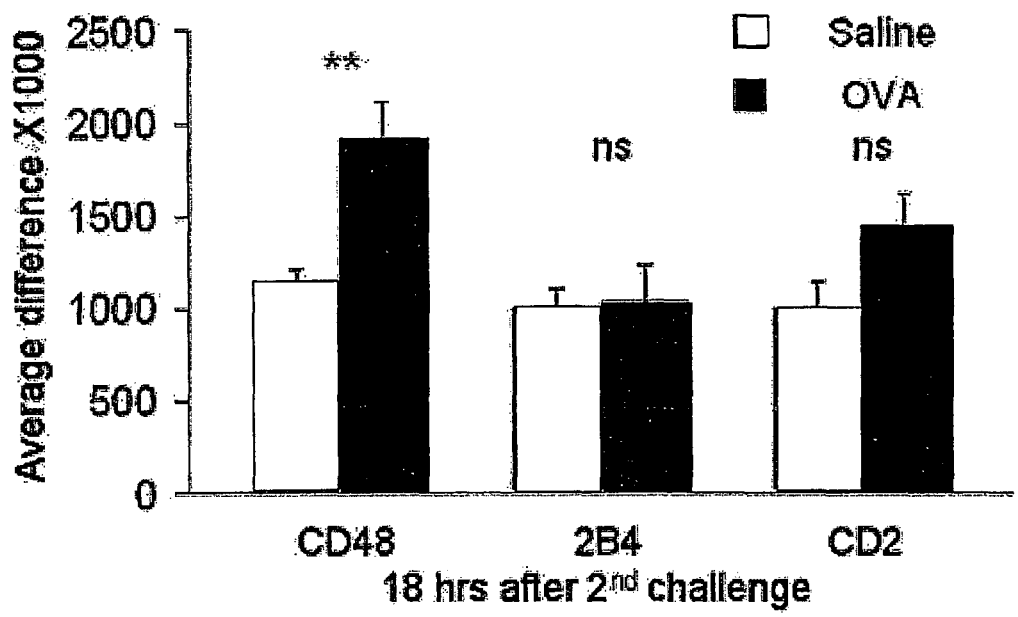
FIG. 1A-1C: DNA Microarray Analysis Identifies CD48 as an Allergen-Induced Gene in Allergic Eosinophilic Airway Inflammation Expression of CD48 in Ovalbumin (OVA) (A) and A. fumigatus-challenged mice (B) as measured by gene chip analysis is shown. The average difference for the hybridization signal after saline (gray bar) and allergen (black bar) challenge is depicted (n=3 for *Aspergillus* control group and n=4 for OVA control group and OVA and *Aspergillus* experimental groups). The induction of CD48 in allergen-challenged mice as measured by Northern blot analysis is shown (C). Total RNA was electrophoresed, transferred and hybridized with a radiolabeled sequence-confirmed CD48 cDNA probe. The location of 18S RNA is shown. Each lane represents an extract from one separate mouse.
Figure 1B:
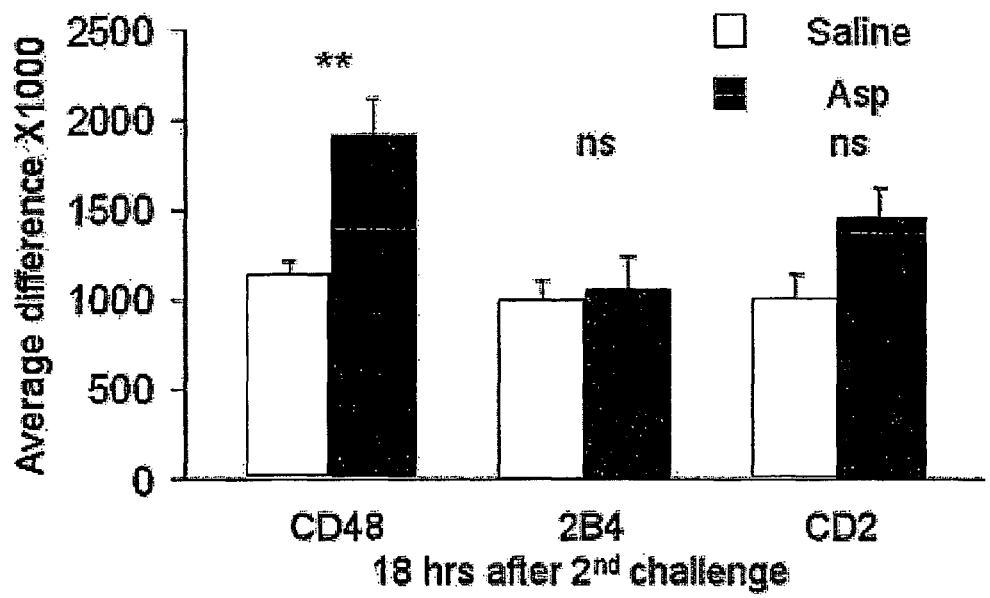
Figure 1C:
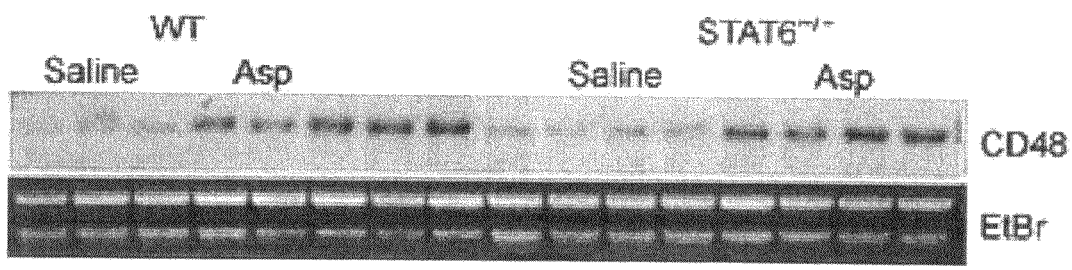

DNA Microarray Analysis Identifies CD48 as an Allergen-Induced Gene in Allergic Eosinophilic Airway Inflammation Quantitative microarray analysis revealed that CD48 but not CD2 or 2B4 mRNA expression was significantly increased in both the OVA- and *Aspergillus*-induced allergic eosinophilic airway inflammation models (FIGS. 1A-B respectively. In the OVA-induced experimental asthma model, kinetic analysis revealed that CD48 mRNA was significantly up-regulated 18 hrs after the second allergen challenge but not after a single allergen challenge or 3 hrs after the second allergen challenge (not shown). In the *Aspergillus*-induced experimental asthma model, CD48 was up-regulated 18 hrs after the ninth allergen challenge. Subsequently, this data was confirmed by Northern Blot analysis. As shown in FIG. 1C there is a low basal expression of CD48 in the lungs of saline treated mice. However, the levels of CD48 were significantly up-regulated after OVA and *Aspergillus* challenge.

Example 2

Peripheral Blood Eosinophils and Nasal Polyp Eosinophils of Atopic Asthmatics Express Increased Levels of CD48

Figure 2A:
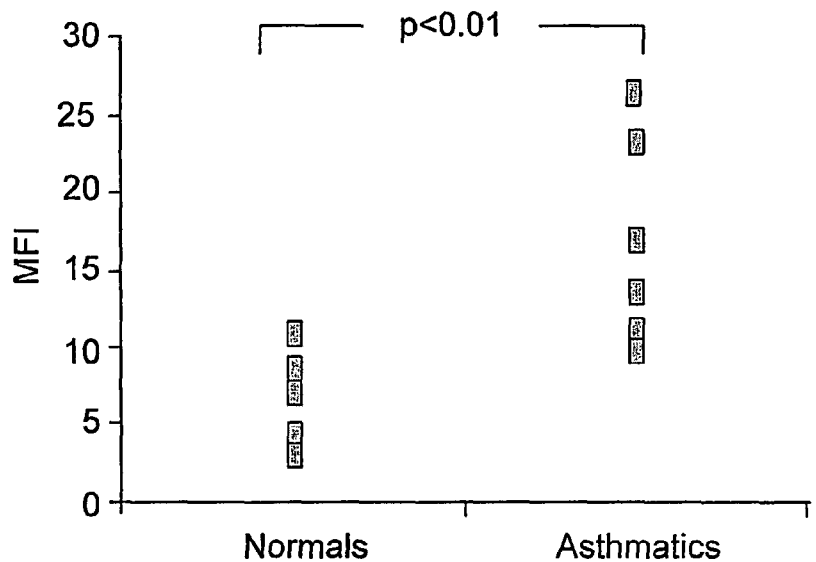
FIG. 2A-2B: Peripheral Blood Eosinophils and Nasal Polyp Eosinophils of Atopic Asthmatics Display Enhanced Levels of CD48 Expression Human peripheral blood eosinophils (A) and human nasal polyp eosinophils (B) from atopic asthmatic (n=7 and 8, respectively) or normal (n=6 and 9, respectively) individuals were stained with anti-CD48 mAb followed by goat anti-mouse FITC and analyzed by FACS. For identification of nasal polyp eosinophils, the cells were additionally stained with rat anti-mouse CCR3 PE. CCR3$^+$/SSC$^{high}$ cells were identified as eosinophils and analyzed for CD48 expression. Data are presented as mean fluorescent intensity (MFI), each dot represents one donor.
Figure 2B:
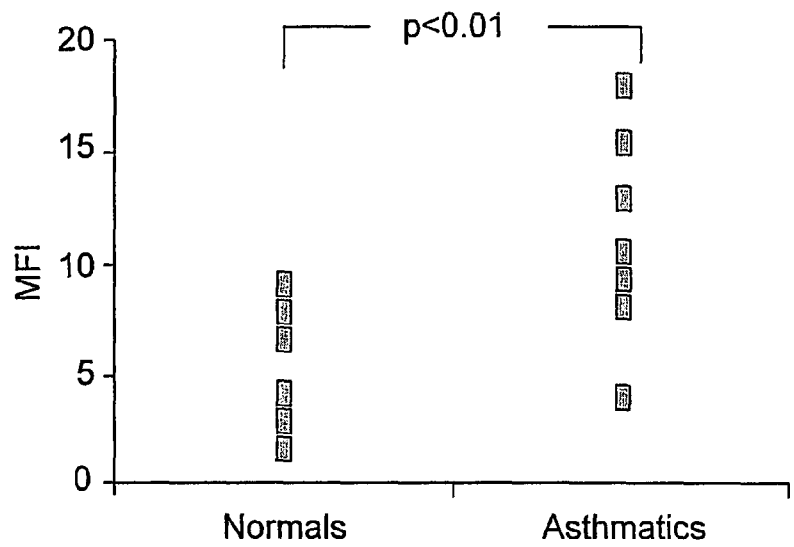

The inventors examined whether CD48 expression on eosinophils is elevated in atopic asthmatic donors compared to normal controls. As assessed by FACS analysis, peripheral blood eosinophils from atopic asthmatic donors expressed higher levels of CD48 (MFI 16.87±6.16, n=7, p<0.01) compared with eosinophils from non-asthmatic donors (MFI 7.07±2.63) (FIG. 2A). Nasal polyposis has been linked to bronchial asthma and the percentage of infiltrating eosinophils in the polyps can reach as high as 60% [Eliashar, R. and Levi-Schaffer (2005) *Curr. Opin. Otolaryngol. Head Neck Surg.* 13: 171-175]. Nasal polyp eosinophils obtained from asthmatic donors demonstrated significantly higher CD48 levels (MFI 10.11±4.26, n=11, p<0.01) than nasal polyp eosinophils from non-asthmatic individuals (MFI 4.68±2.57) (FIG. 2B).

Example 3

The Expression of CD48 on Human Eosinophils is Up-Regulated by IL-3

The observation that human eosinophils from asthmatic donors display elevated levels of CD48 suggests that its expression may be regulated by a mediator involved in asthma pathogenesis. To clarify which mediator may regulate CD48, freshly isolated eosinophils were incubated with cytokines, growth factors and chemokines, including IL-2, IL-3, IL-4, IL-5, IL-8, IL-13, IFN-γ, GM-CSF, SCF, TGF-β, eotaxin-1, RANTES and MIP-1α that are found in the asthmatic milieu. Although IL-3, IL-5 and GM-CSF share a common β chain (βc) that transduces their signal, only IL-3 up-regulated CD48 expression (FIG. 3A). IL-3 elicited its effect in a concentration-dependent fashion, with a maximal effect at 20 ng/ml (1.51±0.13 fold increase, 2.11±0.13 fold increase and 1.91±0.06 fold increase, respectively, following stimulation with 2, 20 or 200 ng/ml of IL-3, n=5, p<0.001). In addition, kinetic analysis revealed that IL-3-induced up-regulation peaked at 24 hours (2.14±0.15 fold increase, n=3, p<0.01) (FIG. 3B).

Example 4

Northern Blot Analysis Indicates that CD48 Expression is Independent of STAT6, IL-4 and IL-13

The demonstration that CD48 has an inducible expression pattern on eosinophils during induction of experimental asthma indicates that there is a factor in the asthmatic milieu that regulates this phenomenon. Asthma is a $Th_2$ associated process, therefore the inventors aimed to determine whether signaling pathways such as STAT6 or cytokines such as IL-4 and IL-13 that are key regulators of the asthmatic response are involved in the up-regulation of CD48. Therefore, OVA- and *Aspergillus*-induced experimental allergic-eosinophilic airway inflammation protocols were employed to STAT6-, IL-13- and IL-4/IL-13 deficient mice. Thereafter, total lung mRNA was extracted and subjected to Northern blot analysis. As shown in FIGS. 4A-D, the up-regulation of CD48 expression was found to be independent of all of these factors in both the OVA- and *Aspergillus*-induced models.

Figure 4A:
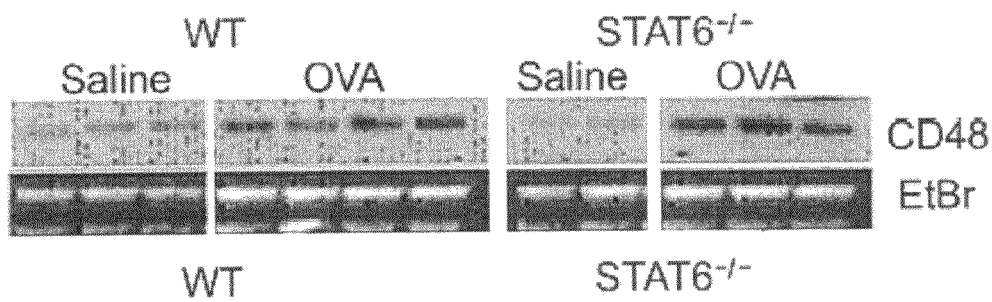
Figure 4B:
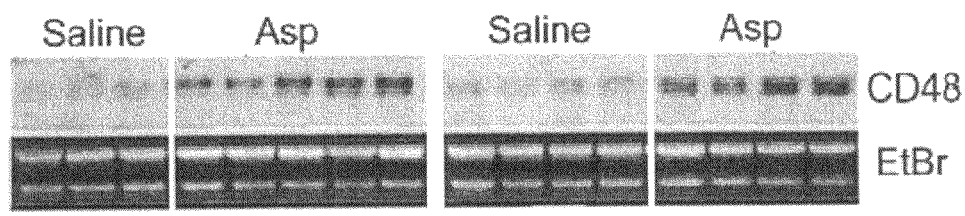
Figure 4C:
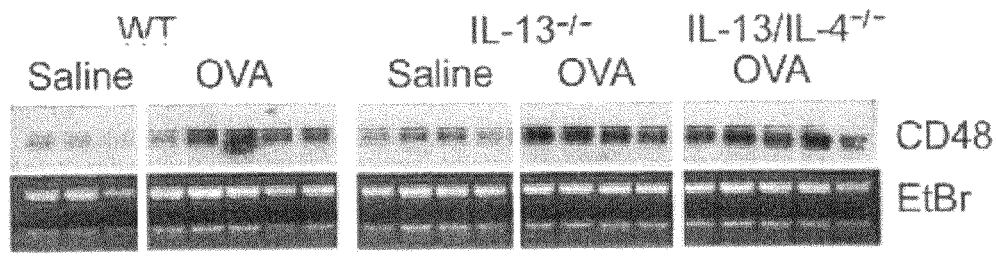
Figure 4D:
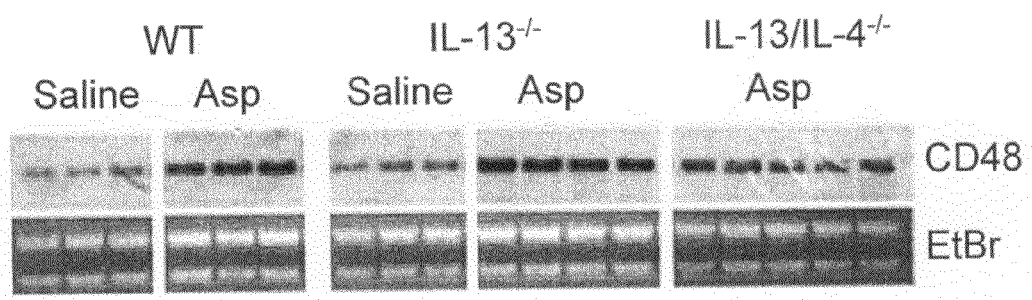
Figure 4E:
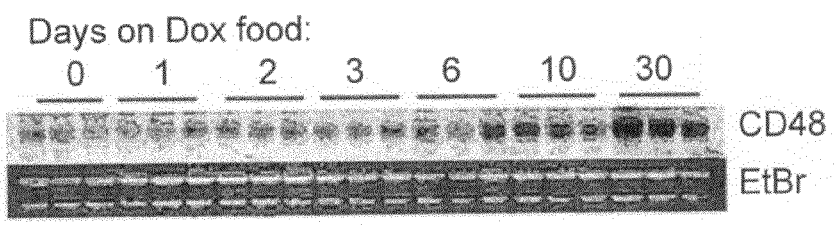

Nevertheless, inducible IL-13 transgenic mice display elevated levels of CD48 starting after 6 days of IL-13 induction, indicating that IL-13 over-expression is sufficient for CD48 overexpression (FIG. 4E).

Example 5

CD48 Activates Human Eosinophils to Release EPO

Expression of CD48 on the eosinophil surface suggests that eosinophil responses may be regulated by this receptor. Cross-linking of CD48 on human eosinophils induced EPO release (FIG. 5). However, CD48 cross-linking did not induce cytokine release, as IL-4, IL-8 and IFN-γ were not detected in the culture supernatants. Furthermore, cross-linking of CD48 in the presence of IL-3 did not enhance EPO release or cause cytokine release (data not shown).

Example 6

IL-3 Regulates CD48 Expression in Mice

Figure 6A:
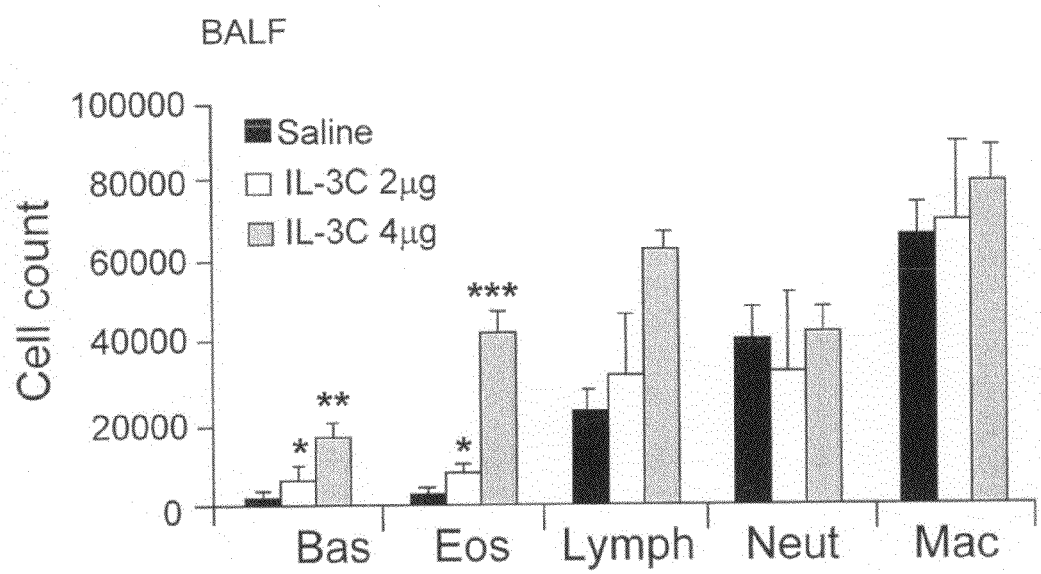
Figure 6B:
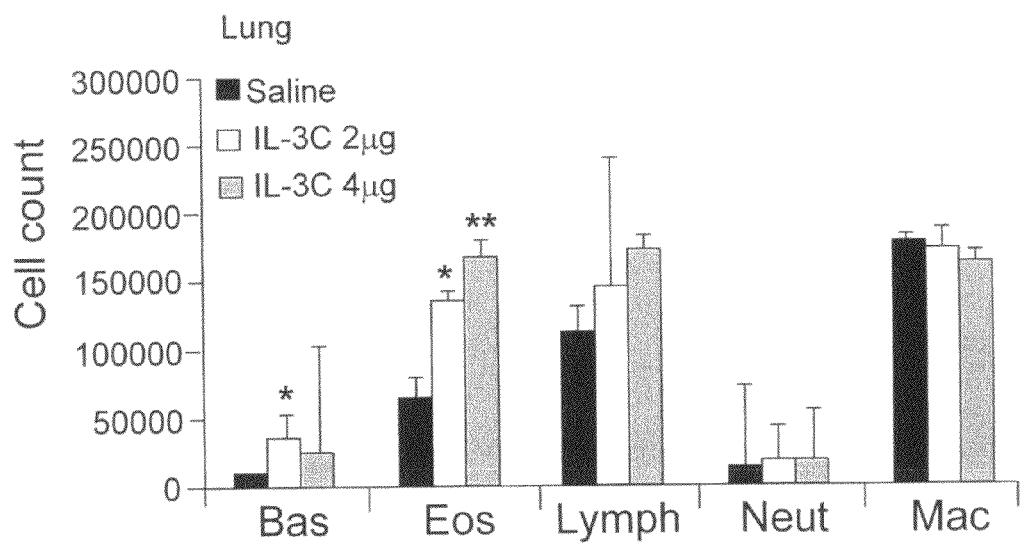
Figure 6C:
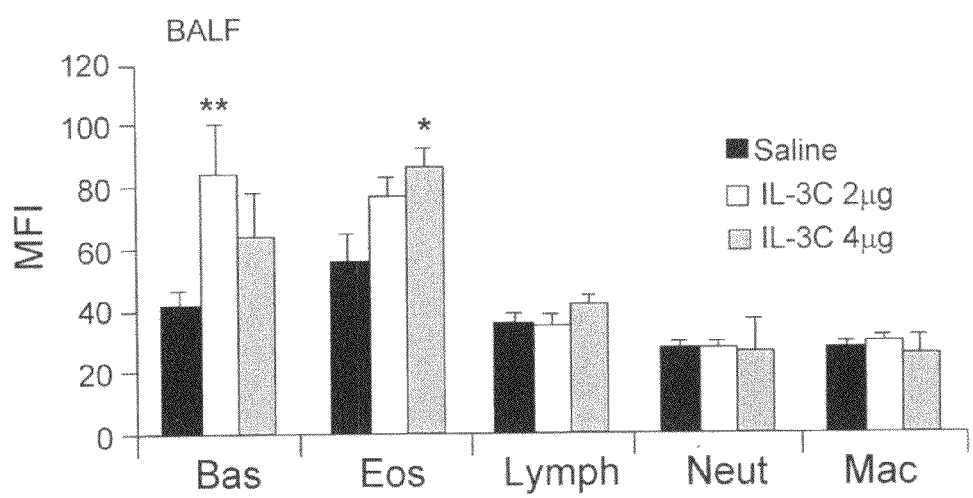
Figure 6D:
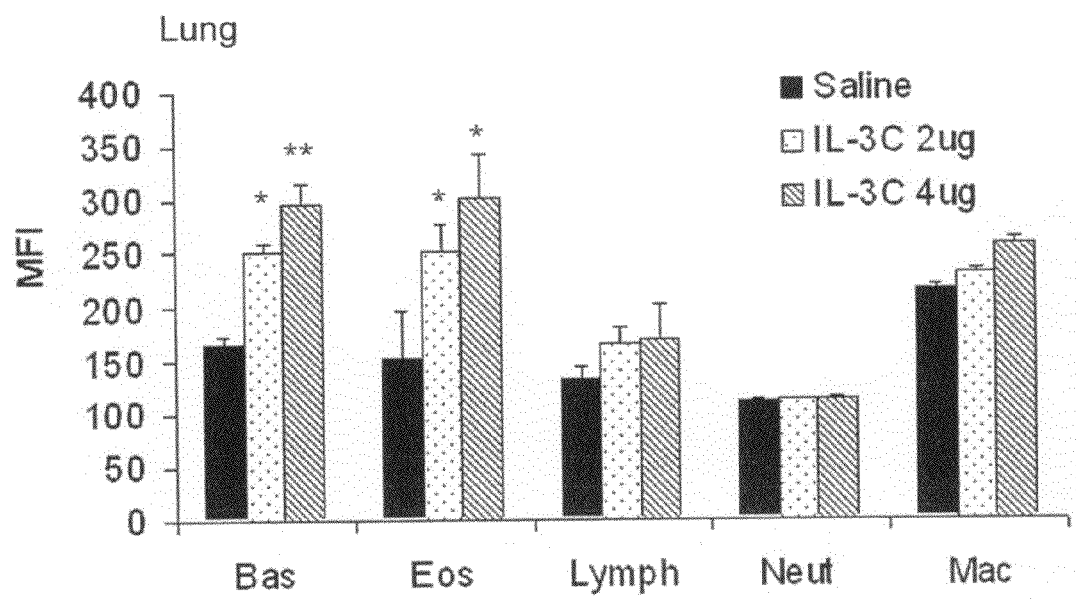
Figure 6E:
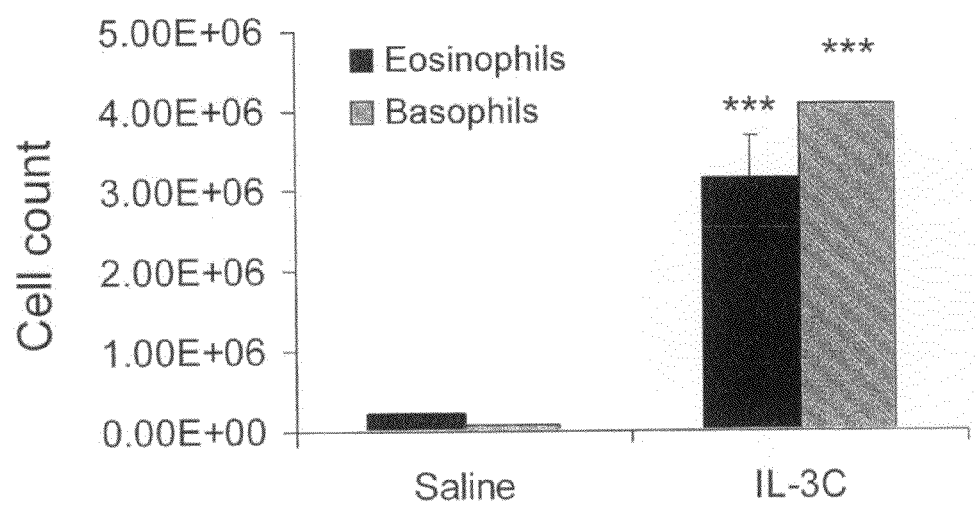
Figure 6F:
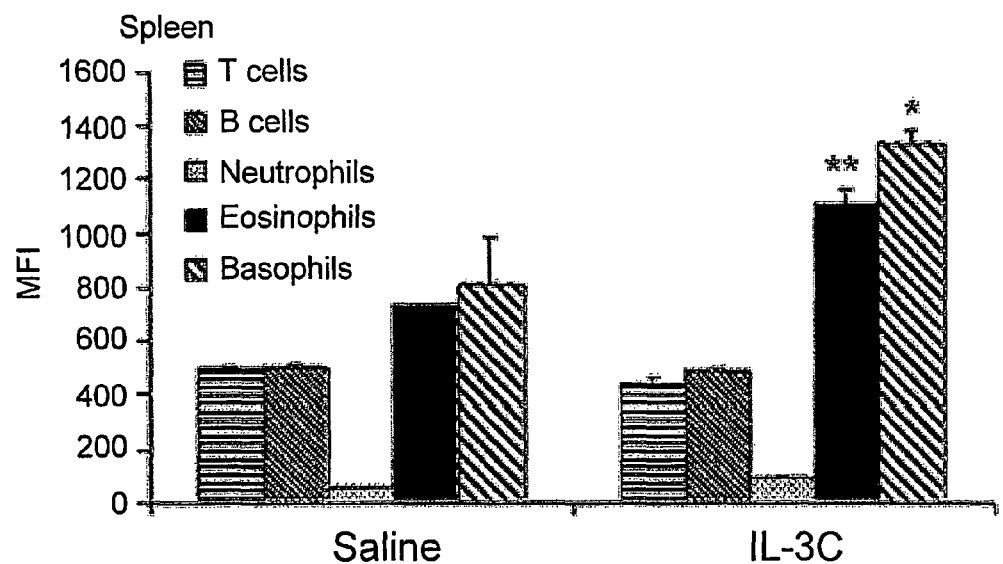

Important effector mechanisms are likely to display conserved regulatory pathways between different species. Thus, the inventors verified whether IL-3 up-regulated CD48 expression in vivo in the mouse. Intranasal administration of IL-3 to BALB/c mice for 21 days significantly increased eosinophil, basophil and lymphocyte infiltration to the BALF and lungs compared with control (saline administration, FIGS. 6A-B). Furthermore, IL-3 specifically up-regulated CD48 expression on BALF and lung eosinophils and basophils, but did not on lymphocytes, neutrophils or macrophages (FIGS. 6C-D). Consistent with this, intravenous administration of IL-3C increased eosinophil and basophil numbers, as well as their CD48 expression in the spleen (FIGS. 6E-F).

In addition, as assessed by an in vivo cytokine capture assay [Finkelman, F. D. and Morris, S. C. (1999) *Int. Immunol.* 11: 1811-1818], systemic administration of IL-3C increased IL-4 production by 20-30 fold (data not shown). Thus, IL-3 activates mediator release in vivo.

Figure 6G:
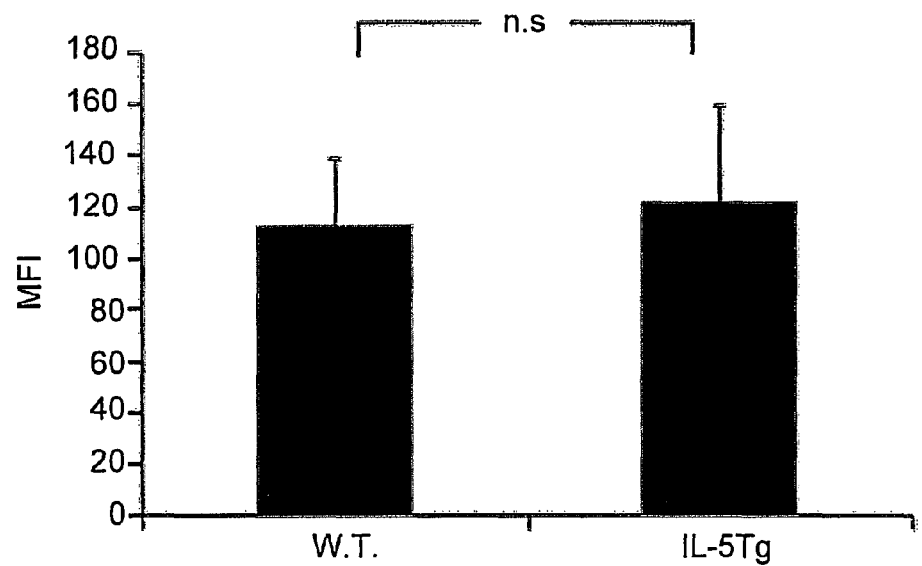

In order to establish whether IL-3 is specifically responsible for CD48 up-regulation in vivo, the expression of CD48 was examined in eosinophils from IL-5 transgenic mice in comparison to wild type mice. As shown in FIG. 6E, eosinophils from IL-5 transgenic mice displayed comparable levels of CD48 compared to wild type mice (FIG. 6G). Therefore, in vivo up-regulation of CD48 expression on mouse eosinophils, like in vitro up-regulation of CD48 on human eosinophils, is induced by IL-3 but not IL-5 in vivo.

Example 7

CD48 is Up-Regulated on Murine Eosinophils in Experimental Asthma and Experimental Allergic Peritonitis Two independent experimental allergy models were examined as to whether CD48 is up-regulated in allergic conditions in mice: in vivo antigen-induced allergic airway inflammation (experimental asthma) and antigen-induced allergic peritonitis. In experimental asthma induced by OVA challenge, expression of CD48 by BALF eosinophils was significantly up-regulated in a time-dependent fashion, while saline challenge had no effect (FIG. 7A). The kinetics of CD48 expression was similar in the BALF and the lungs increasing 6 hrs after the last allergen challenge and peaking at 24 hrs (data not shown). Eosinophil CD48 expression was also increased in allergic peritonitis, increasing at 8 hrs and peaking at 48 hrs (FIG. 7B).

Example 8

Neutralization of IL-3 in Experimental Asthma Reduces CD48 Expression

To determine whether IL-3 is responsible for the elevated expression of CD48 observed in murine experimental asthma, neutralizing antibodies to IL-3 or isotype matched control antibodies were administered to OVA challenged mice. Neutralization of IL-3 in OVA-challenged mice resulted in a 33% decrease ($p<0.05$) in CD48 expression by BALF eosinophils (FIG. 8A), decreased the number of infiltrating BALF eosinophils (FIG. 8B) and attenuated lung inflammation (FIG. 8C) while an isotype-matched control antibody had no effect. In addition, neutralization of IL-3 decreased the levels of IL-4 in the BALF of OVA-challenged mice from $79\pm2.7$ pg/ml to $61\pm4.5$ pg/ml, $p<0.05$, $n=2$ (data not shown).

Example 9

Cellular Source of CD48, CD2 and 2B4 in the Lungs

The inventors next determined the cellular source of CD48 and its ligands. Most of the cells in the lung and BALF expressed CD48; however, eosinophils expressed the highest levels of CD48 and were the main cellular source for its expression comprising ~50-65% of $CD48^+$ cells in the lung (FIG. 9). Interestingly, murine eosinophils did not express 2B4 and 2B4 expression was restricted to NK and NKT cells. In addition, CD2 expression was limited to NKT, NK and $CD4^+$ T cells (FIG. 9).

Example 10

Neutralization of CD48 Attenuates Eosinophilic Inflammation, Th2 and Proinflammatory Cytokines Expression in the BALF The demonstration that CD48 is upregulated in allergic-eosinophilic airway inflammation raised the possibility that this type of inflammation is dependent on CD48 and its ligands. Consequently, the inventors used specific neutralizing antibodies for CD48, CD2 and 2B4 to investigate their roles in this experimental regime (FIGS. 10A-F).

Figure 10A:
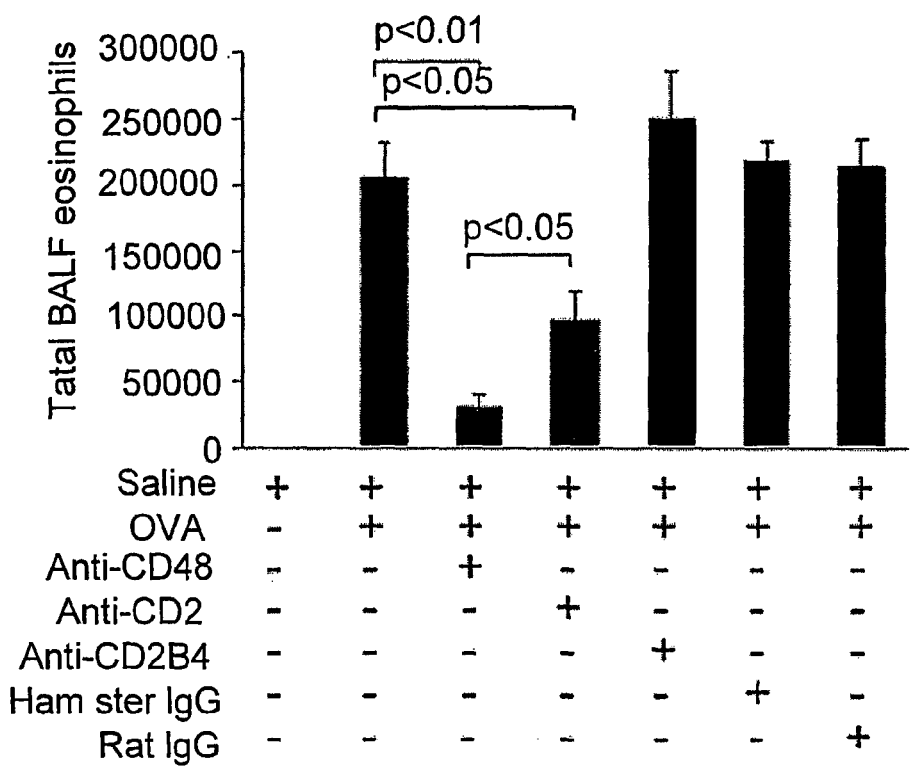
Figure 10B:
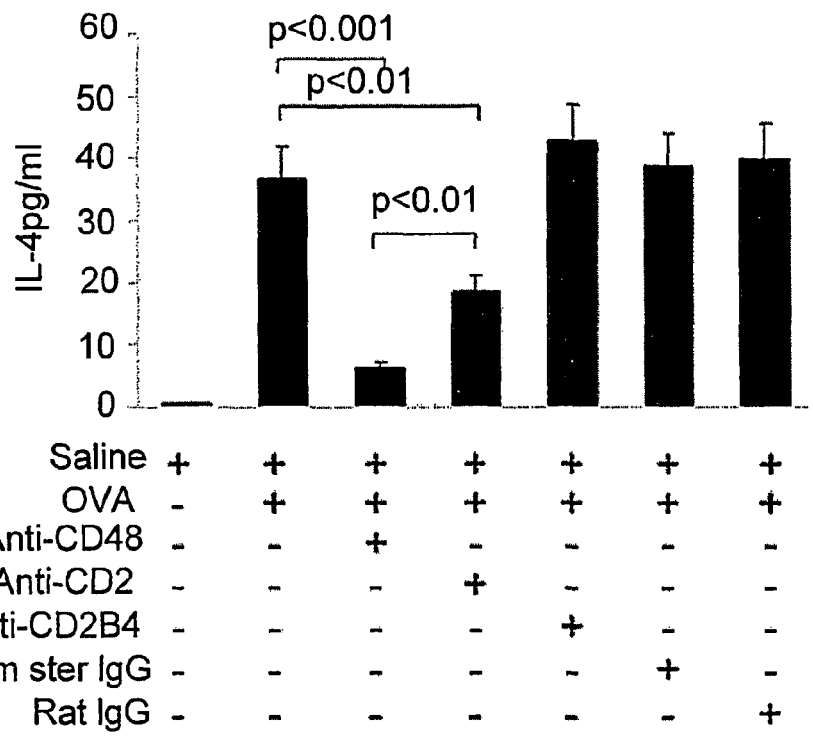
Figure 10C:
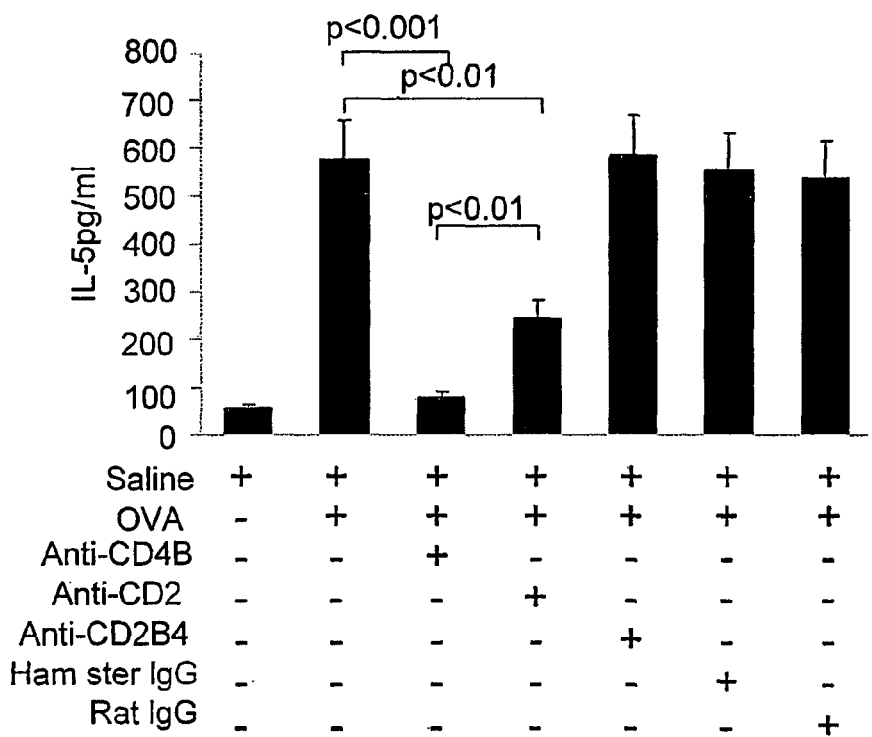
Figure 10D:
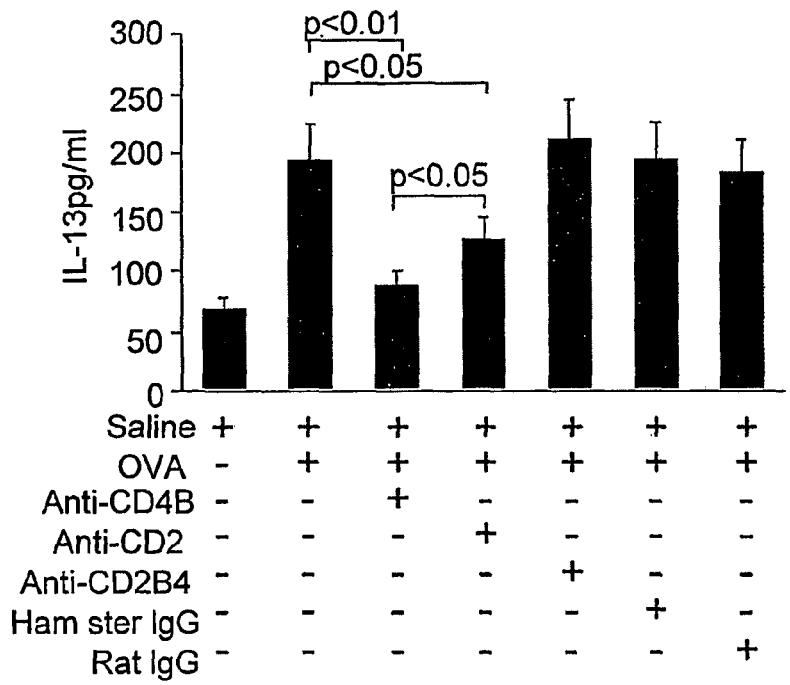
Figure 10E:
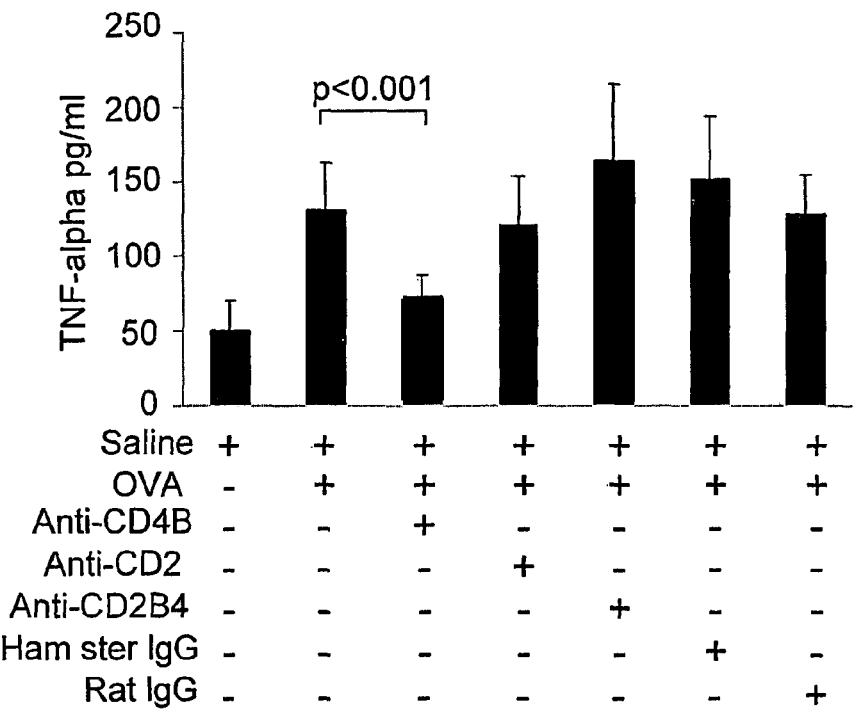
Figure 10F:
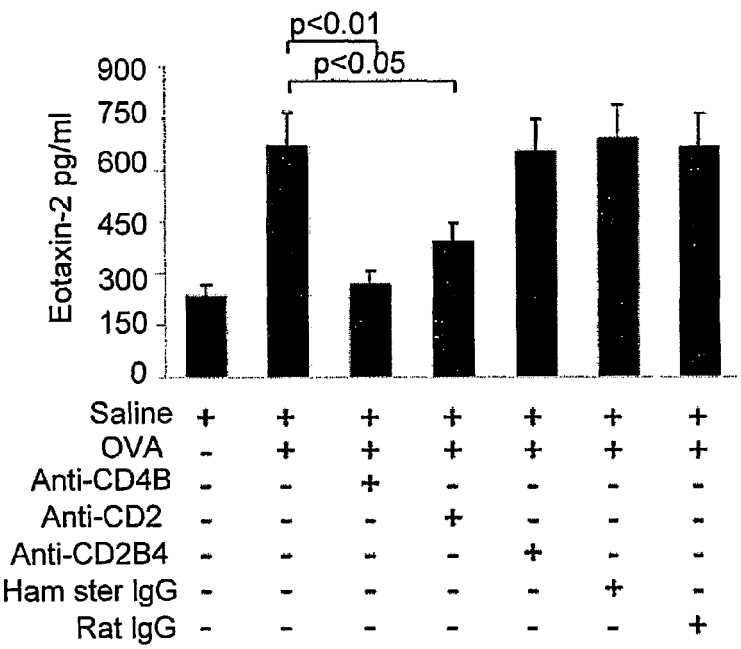

Anti-CD48 mAb treatment prior to allergen challenge considerably reduced BALF inflammation. For example, eosinophilic inflammation was significantly decreased upon CD48 pretreatment (~85%). Interestingly, anti-CD2 mAb pretreatment inhibited BALF inflammation to a lesser extent and caused a ~45% reduction in BALF eosinophils. Pretreatment with anti-2B4 mAb did not alter eosinophilic inflammation (FIG. 10A). In addition, OVA-challenged mice displayed increased IL-4, IL-5, IL-13, TNF-α and eotaxin-2 levels (FIGS. 10B-F). However, mice pretreated with anti-CD48 mAb showed a pronounced reduction of these cytokines (75%-93% decrease). In contrast, mice treated with anti-CD2 or anti-2B4 mAb exhibited only a ~40-50% decrease in the BALF cytokine profile or had no effect, respectively. Notably, all of the aforementioned effects were specific since mice that were treated with control antibodies displayed equivalent cytokine levels to OVA-challenged mice.

Figure 10G:
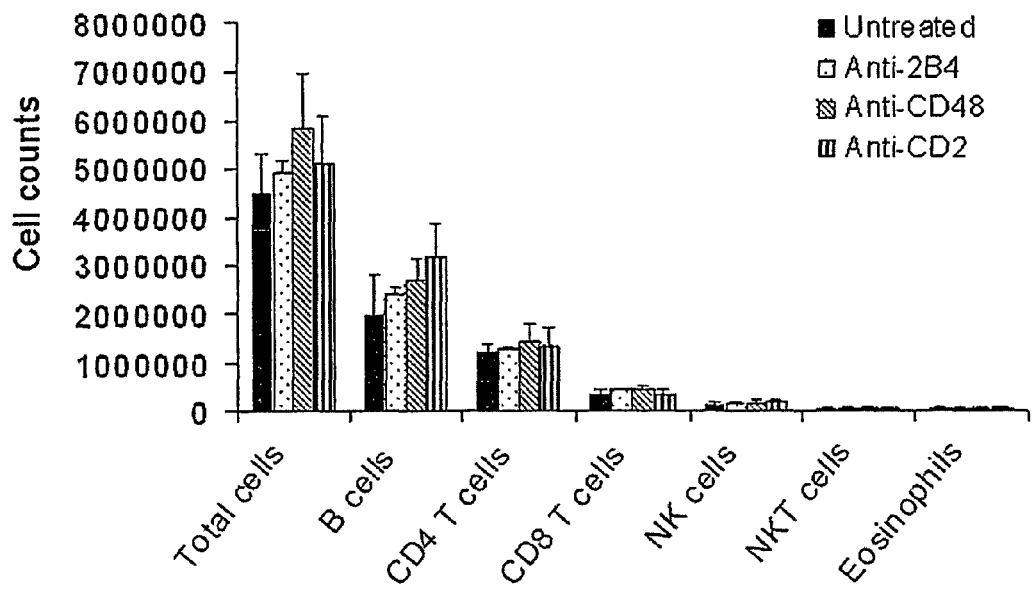
Figure 11A:
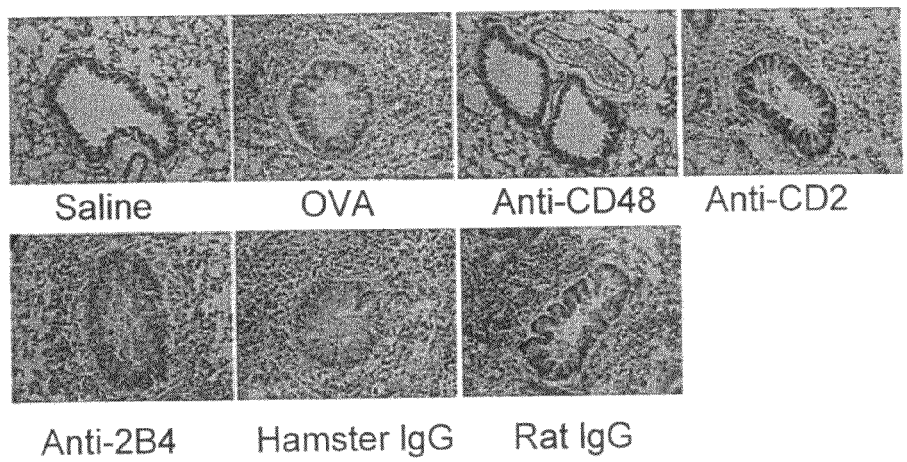
Figure 11B:
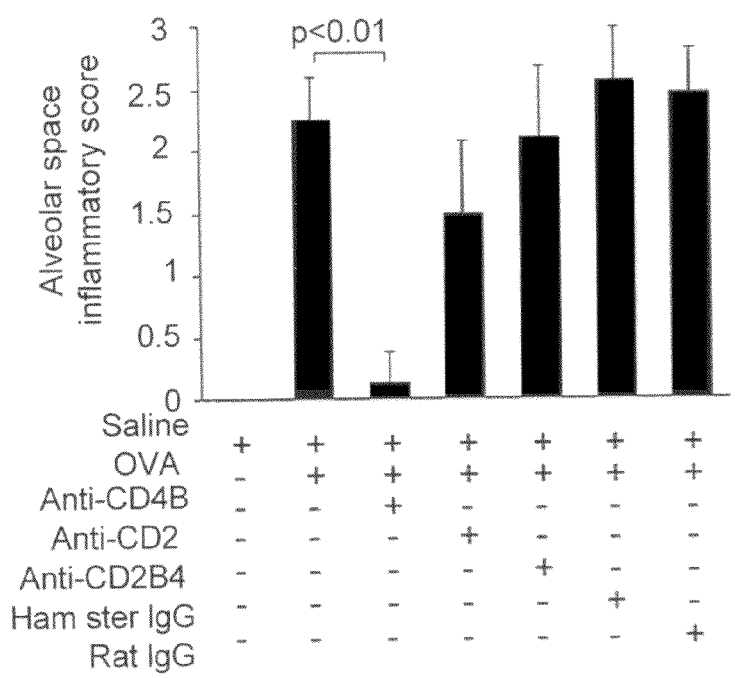
Figure 11C:
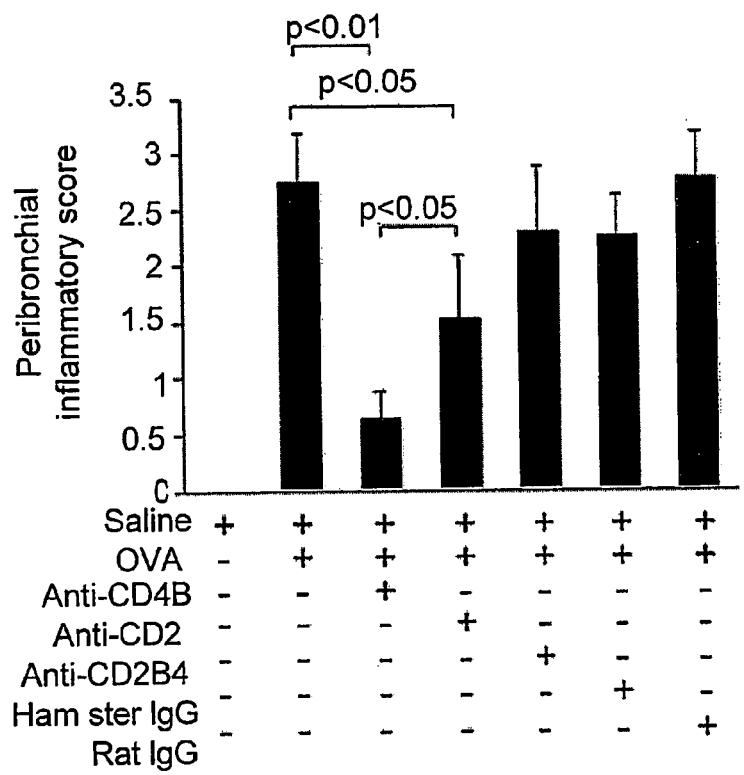
Figure 11D:
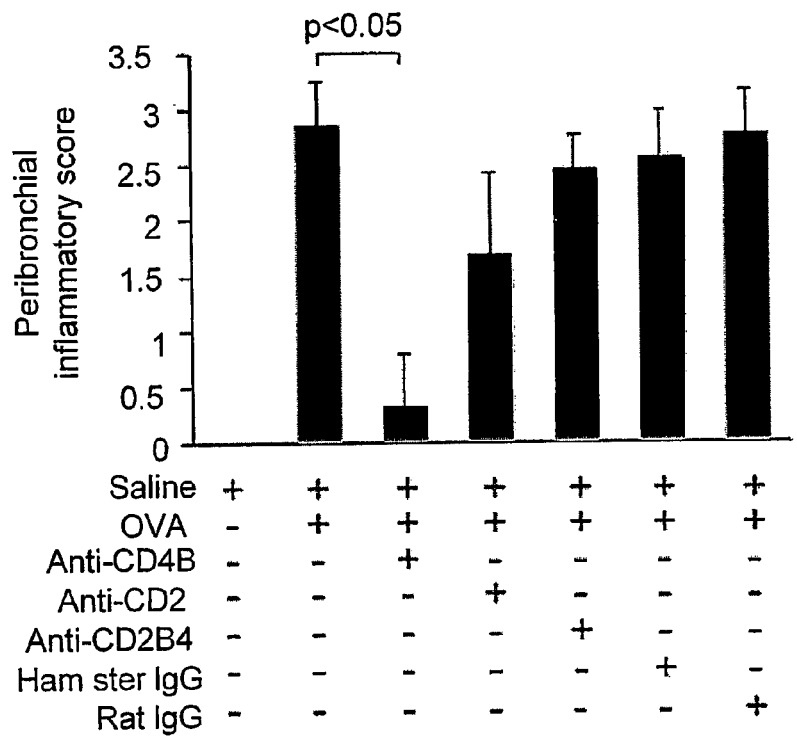

The aforementioned antibodies were also analyzed by us to role out the possibility that they may deplete targeted cells in vivo. As shown by FIG. 10G, administration of anti-CD48, anti-CD2 and anti-2B4 Abs did not alter splenic and peripheral blood cellular composition or numbers.

Example 11

Neutralization of CD48 Attenuates Lung Inflammation

These findings indicate that CD48 has a significant role in the allergen-induced inflammatory response. Accordingly, lung histology followed by quantitative analysis was performed to assess the effects of CD48 and its ligands on several parameters of lung inflammation (FIGS. 11A-D). As shown, OVA challenged mice, displayed evident perivascular and peribronchial eosinophilic inflammation, epithelial damage and airway muscle thickening. Anti-CD48 treated mice had a striking reduction in alveolar space, lung perivascular and peribronchial inflammation and epithelial shedding (FIGS. 11A-D). This effect was specific to CD48 treatment since anti-CD2 treatment induced a mild inhibitory effect only on the peribronchial inflammatory score, and anti-2B4 treatment seemed to enhance lung inflammation. Importantly, control antibodies did not alter these features.

Example 12

Neutralization of CD48 Attenuates Goblet Cell Hyperplasia, Mucus Production and Smooth Muscle Thickening in the Lung.

One of the main features of allergic eosinophilic airway inflammation is mucus production and goblet cell hyperplasia. As assessed by PAS staining, allergen challenge increased goblet cell hyperplasia and mucus production. This effect was significantly reduced by anti-CD48 pretreatment (FIG. 12A-B) but not anti-2B4 treatment while anti-CD2 treatment induced a negligible effect.

In addition, the thickness of the peribronchial smooth muscle layer was significantly greater in OVA-challenged mice than in saline-challenged mice. Anti-CD48 mAb-treated mice displayed significantly less smooth muscle thickening (FIG. 12C). Anti-CD2-treated mice exhibited a minor reduction, while anti-2B4 and control antibodies had no effect.

The invention claimed is:

1. A method of treating an allergic condition, said method comprising administering a therapeutically effective amount of an anti-CD48 agent consisting of (i) an antibody which specifically binds to CD48 or (ii) a CD48 binding fragment of said antibody, which anti-CD48 agent blocks the CD48 stimulatory pathway, to a subject suffering from an allergic condition, wherein said allergic condition is an allergic inflammation selected from the group consisting of allergic airway inflammation, atopic dermatitis, conjunctivitis and intestinal allergy.

2. The method according to claim 1, wherein said allergic airway inflammation is any one of asthma and nasal polyposis.

3. A method of inhibiting the activity and/or expression of CD48 in cells of a subject suffering from an allergic inflammation, said method comprising the step of in vivo contacting said cells with an effective amount of an anti-CD48 agent consisting of (i) an anti-CD48 antibody, (ii) a CD48 binding fragment of said antibody, or (iii) a combination thereof, wherein said allergic inflammation is selected from the group consisting of allergic airway inflammation, atopic dermatitis conjunctivitis and intestinal allergy.

4. The method according to claim 3, wherein said allergic airway inflammation is asthma or nasal polyposis.

5. A method of treating an allergic condition, said method comprising administering a therapeutically effective amount of an anti-CD48 agent consisting of (i) a neutralizing antibody, which specifically binds to CD48, or (ii) a CD48 binding fragment of said neutralizing antibody, which anti-CD48 agent blocks the CD48 stimulatory pathway, to a subject suffering from an allergic condition, wherein said allergic condition is an allergic inflammation selected from the group consisting of allergic airway inflammation, atopic dermatitis, conjunctivitis and intestinal allergy.

6. The method according to claim 5, wherein said allergic airway inflammation is any one of asthma and nasal polyposis.

7. A method of inhibiting the activity and/or expression of CD48 in cells of a subject suffering from an allergic inflammation said method comprising the step of in vivo contacting said cells with an effective amount of an anti-CD48 agent consisting of (i) a neutralizing anti-CD48 antibody, (ii) a CD48 binding fragment of said neutralizing antibody, (iii) a combination thereof, or (iv) a composition comprising the same, wherein said allergic inflammation is selected from the group consisting of allergic airway inflammation, atopic dermatitis, conjunctivitis and intestinal allergy.

8. The method according to claim 7, wherein said allergic airway inflammation is any one of asthma and nasal polyposis.

* * * * *